United States Patent
Shimizu et al.

(10) Patent No.: US 8,106,549 B2
(45) Date of Patent: Jan. 31, 2012

(54) MOTOR AND ENDOSCOPE PROBE EQUIPPED WITH MOTOR

(75) Inventors: Yukiharu Shimizu, Tokyo (JP); Kazuya Nakamura, Tokyo (JP); Tsuyoshi Takano, Tokyo (JP)

(73) Assignee: Namiki Seimitsu Houseki Kabushiki Kaisha (JP)

( * ) Notice: Subject to any disclaimer, the term of this patent is extended or adjusted under 35 U.S.C. 154(b) by 230 days.

(21) Appl. No.: 12/523,974

(22) PCT Filed: Jan. 30, 2008

(86) PCT No.: PCT/JP2008/051334
§ 371 (c)(1),
(2), (4) Date: Jul. 21, 2009

(87) PCT Pub. No.: WO2008/093689
PCT Pub. Date: Aug. 7, 2008

(65) Prior Publication Data
US 2010/0105980 A1    Apr. 29, 2010

(30) Foreign Application Priority Data

Jan. 31, 2007  (JP) .................................. 2007-021906
Mar. 2, 2007   (JP) .................................. 2007-053325

(51) Int. Cl.
*H02K 11/00* (2006.01)
(52) U.S. Cl. ......... 310/71; 310/40 MM; 310/83; 310/89
(58) Field of Classification Search .................... 310/71, 310/40 MM, 83, 89; *H02K 11/00*
See application file for complete search history.

(56) References Cited

U.S. PATENT DOCUMENTS

| 5,240,003 A  | * | 8/1993  | Lancee et al. ............... 600/467 |
| 5,968,416 A  | * | 10/1999 | Smith et al. ................ 252/500 |
| 6,687,010 B1 | * | 2/2004  | Horii et al. ................ 356/479 |
| 2004/0032345 A1 | * | 2/2004 | Kazuya et al. ............... 341/15 |

(Continued)

FOREIGN PATENT DOCUMENTS

JP    2000-166157 A    6/2000
(Continued)

OTHER PUBLICATIONS

International Search Report; PCT/JP2008/051334; Mar. 25, 2008.

*Primary Examiner* — Quyen Leung
*Assistant Examiner* — John K Kim
(74) *Attorney, Agent, or Firm* — Studebaker & Brackett PC; Donald R. Studebaker

(57) ABSTRACT

A motor which can be mounted in an endoscope probe without bending an electric power supply wire in an endoscope probe body, and an endoscope probe using the motor are provided. The motor includes a magnet, a field coil, a housing, an electric power supply wire, and a shaft. A lead wire from the field coil is connected to the electric power supply wire. A cutout is provided in a housing end, and the electric power supply wire is received along the cutout and led out to the outside of the motor in the direction in which a shaft projects. When the motor is mounted in the endoscope probe, the motor is placed in the endoscope probe body so that the shaft projects in the direction opposite to the direction of the front end of the endoscope probe, and the electric power supply wire, which is led out to the outside of the motor, is routed along the longitudinal direction of the endoscope probe.

36 Claims, 31 Drawing Sheets

U.S. PATENT DOCUMENTS

| | | | |
|---|---|---|---|
| 2005/0143664 A1* | 6/2005 | Chen et al. | 600/478 |
| 2007/0000678 A1* | 1/2007 | Yamada et al. | 174/36 |
| 2007/0267934 A1* | 11/2007 | Fukushima et al. | 310/261 |
| 2009/0031839 A1* | 2/2009 | Shimizu et al. | 74/421 A |
| 2010/0105980 A1* | 4/2010 | Shimizu et al. | 600/101 |

FOREIGN PATENT DOCUMENTS

| | | | |
|---|---|---|---|
| WO | WO 2006059461 A1 * | 6/2006 | |
| WO | 2006-118022 A1 | 11/2006 | |

* cited by examiner (a)

(b)

(a)

(b)

(a)

(b)

MOTOR AND ENDOSCOPE PROBE EQUIPPED WITH MOTOR

TECHNICAL FIELD

The present invention relates to a motor used in an endoscope probe and an endoscope probe equipped with the motor.

RELATED ART

Recently, as the use of an image in diagnosis has spread, importance of a technique for measuring internal information of a subject in a non-invasive or non-contact manner has been gradually increased.

Conventionally, the non-invasive or non-contact measurement of the internal information of the subject such as an organism was mainly performed by X-rays. However, if the X-rays are used, a problem such as exposure to radiation occurs or imaging of a biometric function is hard to be achieved. Accordingly, observation of a tissue inside a body cavity by an ultrasonic endoscope probe has been performed.

However, since the ultrasonic endoscope probe has low spatial resolution, information such as physiologic compositions other than a shape cannot be obtained. In addition, when the ultrasonic endoscope probe is used, since a medium such as water is required, a process of observing the subject is troublesome.

Accordingly, recently, a variety of techniques related to Optical Coherence Tomography (OCT) of making internal information of a subject visible using light has been suggested. For example, the related art is disclosed in Patent Document 1. An OCT endoscope probe is inserted into a body cavity organ and OCT scanning is then performed, such that tomogram of an organ wall is acquired.
Patent Document 1: US2005/0143664

In order to perform the scanning of the light necessary for observing the tomogram by a simple operation with certainty, in Patent Document 1, as shown in FIG. 22, an OCT endoscope probe 100 (hereinafter, referred to as a probe 100 if necessary) in which a motor 101 with a small diameter is placed on a probe front end 102 is formed. In addition, an optical fiber 103 faces a shaft 104 of the motor 101, and a prism or mirror is fixed to the end of the shaft 104 as a scanner 105 for reflecting light emitted from the optical fiber 103 at an inclination angle of 45 degrees (in FIG. 22, an embodiment of the prism is shown). In Patent Document 1, by reflecting the light emitted from the optical fiber 103 at the surface of the scanner 105 at 90 degrees and rotating the shaft 104, an optical path is changed by an angle of 90 degrees to an optical axis direction of the optical fiber 103 so as to perform OCT scanning of the inside of a subject.

DISCLOSURE OF THE INVENTION

Problems to be Solved by the Invention

However, in the configuration of the OCT endoscope probe 100 shown in FIG. 22, since the motor 101 is mounted in the OCT endoscope probe 100 such that the end of the shaft 104 faces the end of the optical fiber 103, an electric power supply portion of the motor 101 is placed on the side of the front end 102 of the body of the OCT endoscope probe 100.

Accordingly, in order to supply electric power to the motor 101, an electric power supply wire led out from the electric power supply portion in the probe 100 is routed in the direction opposite to the side of the front end 102 and is electrically connected to a power supply for the motor 101 (not shown) placed on the side of the other end of the probe 100. However, in order to route the electric power supply wire in the probe 100, as schematically shown in FIG. 23, the electric power supply wire 106 is led out in the diameter direction of the motor 101 once and the electric power supply wire 106 needs to be bent.

Accordingly, the electric power supply wire 106 is disconnected at a bent portion or R (corner R) is generated in the electric power supply wire 106 at the bent portion due to bending. The diameter of the probe 100 is increased by amount of the corner R and the length of an inflexible portion of the front end 102 of the probe is increased.

Accordingly, it is an object of the present invention for a motor which can be mounted in an endoscope probe without bending an electric power supply wire and an endoscope probe using the motor.

Means for Solving the Problems

A motor described in claim 1 of the present invention includes a magnet, a field coil, a housing, an electric power supply wire, and a shaft, a lead wire led out from the field coil is connected to the electric power supply wire, a cutout is formed in an end of the housing, and the electric power supply wire connected with the lead wire is received along the cutout and led out to the outside of the motor in the direction in which the shaft projects.

A motor described in claim 2 includes a magnet, a field coil, a housing, a flange, an electric power supply wire, and a shaft, a lead wire led out from the field coil is connected to the electric power supply wire, a cutout is formed in an end of the housing, and the electric power supply wire connected with the lead wire is received along the cutout, a flat portion is formed on an outer circumferential surface of the flange, and the electric power supply wire is placed on the flat portion, and the flange on which the electric power supply wire is placed is fixed to an end of the housing, and the electric power supply wire is led out to the outside of the motor in the direction in which the shaft projects.

The motor described in claim 3 is the motor according to claim 1 in which flanges are respectively fixed to one end and the other end of the housing, and one or both of the flanges functions as a shaft bearing.

The motor described in claim 4 is the motor according to claim 2 in which another flange is fixed to an end other than the end of the housing, to which the flange is fixed, and one or both of the flanges functions as a shaft bearing.

The motor described in claim 5 is the motor according to claim 2 in which the electric power supply wire is led out from one side of the outer circumference of the motor.

The motor described in claim 6 is the motor according to claim 1 in which at least a portion of the electric power supply wire is formed of a transparent electrode material.

The motor described in claim 7 is the motor according to claim 2 in which at least a portion of the electric power supply wire is formed of a transparent electrode material.

The motor described in claim 8 is the motor according to claim 1 in which the end of the shaft is obliquely formed to the axial direction of the shaft, and a reflective film is formed on an obliquely formed surface of the shaft such that a light reflection surface is formed in the obliquely formed surface.

The motor described in claim 9 is the motor according to claim 2 in which the end of the shaft is obliquely formed to the axial direction of the shaft, and a reflective film is formed on an obliquely formed surface of the shaft such that a light reflection surface is formed in the obliquely formed surface.

The motor described in claim 10 is the motor according to claim 1 in which the end of the shaft is obliquely formed to the axial direction of the shaft, and an obliquely formed surface of the shaft is mirror-polished such that a light reflection surface is formed in the obliquely formed surface.

The motor described in claim 11 is the motor according to claim 2 in which the end of the shaft is obliquely formed to the axial direction of the shaft, and an obliquely formed surface of the shaft is mirror-polished such that a light reflection surface is formed in the obliquely formed surface.

The motor described in claim 12 is the motor according to claim 1 in which the end of the shaft is obliquely formed to the axial direction of the shaft, and an obliquely formed surface of the shaft is mirror-polished and a reflective film is formed on the obliquely formed surface such that a light reflection surface is formed in the obliquely formed surface.

The motor described in claim 13 is the motor according to claim 2 in which the end of the shaft is obliquely formed to the axial direction of the shaft, and an obliquely formed surface of the shaft is mirror-polished and a reflective film is formed on the obliquely formed surface such that a light reflection surface is formed in the obliquely formed surface.

The motor described in claim 14 is the motor according to claim 1 in which the overall shaft is formed of amorphous metal alloy, the end of the shaft is obliquely formed to the axial direction of the shaft such that a light reflection surface is formed in an obliquely formed surface of the shaft, and the surface roughness Ry of the reflection surface is set to 0.4 μm or less.

The motor described in claim 15 is the motor according to claim 2 in which the overall shaft is formed of amorphous metal alloy, the end of the shaft is obliquely formed to the axial direction of the shaft such that a light reflection surface is formed in an obliquely formed surface of the shaft, and the surface roughness Ry of the reflection surface is set to 0.4 μm or less.

The motor described in claim 16 is the motor according to claim 1 in which the overall shaft is formed of amorphous metal alloy, the end of the shaft is obliquely formed to the axial direction of the shaft, the surface roughness Ry of an obliquely formed surface of the shaft is set to 0.4 μm or less, and a reflective film is formed on the obliquely formed surface of the shaft such that a light reflection surface is formed in the obliquely formed surface.

The motor described in claim 17 is the motor according to claim 2 in which the overall shaft is formed of amorphous metal alloy, the end of the shaft is obliquely formed to the axial direction of the shaft, the surface roughness Ry of an obliquely formed surface of the shaft is set to 0.4 μm or less, a reflective film is formed on the obliquely formed surface of the shaft such that a light reflection surface is formed in the obliquely formed surface.

A motor described in claim 18 includes a magnet, a field coil, a housing, an electric power supply wire, and a shaft, a lead wire led out from the field coil is connected to the electric power supply wire, a cutout is formed in an end of the housing, the electric power supply wire connected with the lead wire is received along the cutout, the motor further includes a reduction gear head, a pinion is formed on an end of the shaft, and the gear head is driven by and connected to the motor via the pinion, and the electric power supply wire is led out to the outside of the motor in the direction in which the shaft projects.

A motor described in claim 19 a magnet, a field coil, a housing, a flange, an electric power supply wire, and a shaft, a lead wire led out from the field coil is connected to the electric power supply wire, a cutout is formed in an end of the housing, the electric power supply wire connected with the lead wire is received along the cutout, a flat portion is formed on an outer circumferential surface of the flange, and the electric power supply wire is placed on the flat portion, the flange on which the electric power supply wire is placed is fixed to an end of the housing, the motor further includes a reduction gear head, a pinion is formed on an end of the shaft, and the gear head is driven by and connected to the motor via the pinion, and the electric power supply wire is led out to the outside of the motor in the direction in which the shaft projects.

The motor described in claim 20 is the motor according to claim 18 in which the outer diameter of the gear head is less than that of the motor.

The motor described in claim 21 is the motor according to claim 19 in which the outer diameter of the gear head is less than that of the motor.

The motor described in claim 22 is the motor according to claim 18 in which a groove for receiving the electric power supply wire is formed in the housing of the gear head, and the electric power supply wire is received in the groove, and the electric power supply wire is led out to the outside of the motor in the direction in which an output shaft of the gear head projects.

The motor described in claim 23 is the motor according to claim 19 in which a groove for receiving the electric power supply wire is formed in the housing of the gear head, and the electric power supply wire is received in the groove, and the electric power supply wire is led out to the outside of the motor in the direction in which an output shaft of the gear head projects.

The motor described in claim 24 is the motor according to claim 18 in which the end of the output shaft is obliquely formed to the axial direction of the output shaft, and a reflective film is formed on an obliquely formed surface of the output shaft such that a light reflection surface is formed in the obliquely formed surface.

The motor described in claim 25 is the motor according to claim 19 in which the end of the output shaft is obliquely formed to the axial direction of the output shaft, and a reflective film is formed on an obliquely formed surface of the output shaft such that a light reflection surface is formed in the obliquely formed surface.

The motor described in claim 26 is the motor according to claim 18 in which the end of the output shaft is obliquely formed to the axial direction of the output shaft, and an obliquely formed surface of the output shaft is mirror-polished such that a light reflection surface is formed in the obliquely formed surface.

The motor described in claim 27 is the motor according to claim 19 in which the end of the output shaft is obliquely formed to the axial direction of the output shaft, and an obliquely formed surface of the output shaft is mirror-polished such that a light reflection surface is formed in the obliquely formed surface.

The motor described in claim 28 is the motor according to claim 18 in which the end of the output shaft is obliquely formed to the axial direction of the output shaft, and an obliquely formed surface of the output shaft is mirror-polished and a reflective film is formed on the obliquely formed surface such that a light reflection surface is formed in the obliquely formed surface.

The motor described in claim 29 is the motor according to claim 19 in which the end of the output shaft is obliquely formed to the axial direction of the output shaft, and an obliquely formed surface of the output shaft is mirror-polished and a reflective film is formed on the obliquely formed surface such that a light reflection surface is formed in the obliquely formed surface.

The motor described in claim 30 is the motor according to claim 18 in which the overall output shaft is formed of amorphous metal alloy, the end of the output shaft is obliquely formed to the axial direction of the output shaft such that a light reflection surface is formed in an obliquely formed surface of the output shaft, and the surface roughness Ry of the reflection surface is set to 0.4 µm or less.

The motor described in claim 31 is the motor according to claim 19 in which the overall output shaft is formed of amorphous metal alloy, the end of the output shaft is obliquely formed to the axial direction of the output shaft such that a light reflection surface is formed in an obliquely formed surface of the output shaft, and the surface roughness Ry of the reflection surface is set to 0.4 µm or less.

The motor described in claim 32 is the motor according to claim 18 in which the overall output shaft is formed of amorphous metal alloy, the end of the output shaft is obliquely formed to the axial direction of the output shaft, the surface roughness Ry of an obliquely formed surface of the output shaft is set to 0.4 µm or less, and a reflective film is formed on the obliquely formed surface of the output shaft such that a light reflection surface is formed in the obliquely formed surface.

The motor described in claim 33 is the motor according to claim 19 in which the overall output shaft is formed of amorphous metal alloy, the end of the output shaft is obliquely formed to the axial direction of the output shaft, the surface roughness Ry of an obliquely formed surface of the output shaft is set to 0.4 µm or less, a reflective film is formed on the obliquely formed surface of the output shaft such that a light reflection surface is formed in the obliquely formed surface.

An endoscope probe described in claim 34 includes the motor according to any one of claims 1 to 33, the motor is placed in the endoscope probe body such that the shaft or the output shaft projects in the direction opposite to the direction of the front end of the endoscope probe, and the electric power supply wire led out to the outside of the motor is routed along the longitudinal direction of the endoscope probe.

Effect of the Invention

According to claims 1, 2, 18, 19 and 34 of the present invention, since the electric power supply wire is led out in the direction in which the shaft of the motor projects or the direction in which the output shaft of the gear head projects, when the motor is mounted in the endoscope probe and the electric power supply wire is routed in the endoscope probe body, the electric power supply wire may not be bent. Accordingly, it is possible to prevent disconnection of the electric power supply wire and solve generation of R (corner R) of a bent portion generated due to bending. Therefore, it is possible to suppress the increase in diameter of the endoscope probe and to shorten an inflexible portion of the front end of the endoscope probe.

According to the motor described in claim 1, since the electric power supply wire is received in the cutout and led out to the outside of the motor, it is possible to prevent protrusion of the electric power supply wires in the diameter direction of the motor. Even in this case, it is possible to suppress the increase in diameter of the endoscope probe.

According to the motor described in claim 2, since the flat portion is formed on the outer circumferential surface of the flange and the electric power supply wire is placed on the flat portion, it is possible to prevent protrusion of the electric power supply wires in the diameter direction of the motor. Therefore, it is possible to suppress the increase in diameter of the probe.

According to the motor described in claim 3 or 4, since the flange functions as the shaft bearing, the number of parts included in the diameter direction of the motor can be reduced and thus the motor and the endoscope probe can be further downsized.

According to the motor described in claim 5, since the electric power supply wire is led out from only the circumference of one side of the motor to the outside of the motor, the number of electric power supply wires which become an obstacle at the time of scanning of the probe can be reduced and thus the rotation angle of the scanning shaft or output shaft is enlarged.

According to the motor described in claim 6 or 7, when the endoscope probe is scanned at a rotation angle of 360 degrees, it is possible to prevent the electric power supply wire of the motor from becoming an obstacle to scanning.

According to the motor described in claim 20 or 21, the electric power supply wire led out from the motor does not protrude in the outer diameter direction of the motor in the outer circumference of the gear head and the electric power supply wire can be led out to the outside of the motor in the direction in which the output shaft of the gear head projects. Therefore, it is possible to suppress the increase in diameter of the endoscope probe.

According to the motor described in claim 22 or 23, since the groove for receiving the electric power supply wire is formed in the housing of the gear head, the electric power supply wire is received in the groove, and the electric power supply wire is led out to the outside of the motor in the direction in which the output shaft of the gear head projects, it is possible to prevent protrusion of the electric power supply wire to the outer circumference of the gear head even when the outer diameter of the gear head is set to at least the outer diameter of the motor. Therefore, it is possible to suppress the increase in diameter of the endoscope probe.

According to the motor described in any one of claims 8 to 17 or 24 to 33, since the end of the shaft or the end of the output shaft of the motor is formed of the light reflection surface, an optical part for a scanner, such as a mirror or a prism, is unnecessary in the end of the shaft or the end of the output shaft. Accordingly, a space occupied by the scanner in the internal space of the front end of the probe can be eliminated and the inflexible portion of the front end of the OCT endoscope probe can be shortened. In addition, the number of parts can be reduced.

Since the light reflection surface is directly formed in the end of the shaft or the end of the output shaft, further, the optical path of the light after being reflected from the reflection surface can be set by desire and efficient light transmission to the subject can be achieved.

In addition, since a separate part such as the optical part for the scanner is not attached to the shaft or the output shaft, it is possible to rotate the shaft or the output shaft with low torque and suppress the increase in size of the motor. Accordingly, it is possible to suppress the increase in diameter of the overall OCT endoscope probe.

By removing the optical part for the scanner, it is possible to reduce one axial shift element between the core axis of the optical fiber and axis of the motor.

According to the motor described in claim 8, 9, 24, 25, 10, 11, 26 or 27, by forming the reflective film on the end of the shaft or the end of the output shaft or performing mirror polishing, the light reflection efficiency of the end of the shaft or the end of the output shaft is improved and thus light propagation efficiency is also improved.

According to the motor described in claim 14, 15, 30 or 31, since the overall shaft or output shaft is formed of amorphous metal alloy, due to the characteristics of the amorphous metal alloy without a crystal grain boundary, it is possible to improve surface smoothness of the reflection surface. Accordingly, since the amorphous metal alloy has a good mold transfer property in the injection molding process or a good polishing property in the polishing process, surface smoothness is excellent. As a result, the reflection efficiency of the manufactured reflection surface is also improved and the light propagation efficiency is also improved.

According to the motor described in claim 12, 13, 16, 17, 28, 29, 32 or 33, the obliquely formed surface on which the reflective film is formed is mirror-formed and the reflective film is then formed. Accordingly, it is possible to further improve the reflection efficiency of the reflection surface.

REFERENCE NUMERALS

Figure 1:
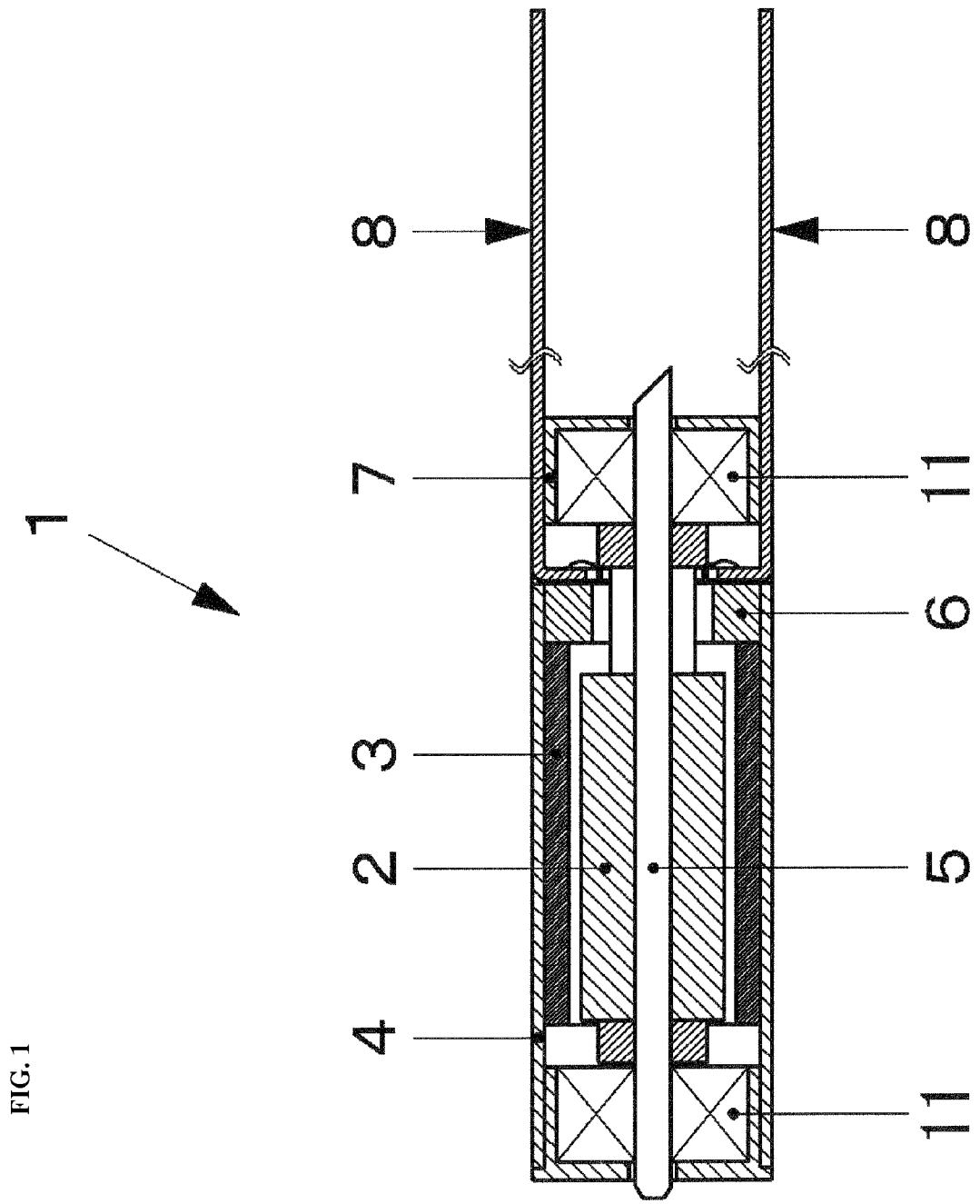
FIG. 1 is a cross-sectional view of a motor according to a first embodiment of the present invention.

1, 18, 44: motor
2: magnet
3: field coil
4, 19, 45: (motor) housing
5: shaft
6, 20: lead wire guide
7, 21, 28: flange
8, 22, 23, 22a: flexible substrate
9: tap wire
10: groove
11: shaft bearing
12: twisted wire
13, 29: electric power supply land
14: reflective film
15: OCT endoscope probe
16: single-mode optical fiber
17: graded-index optical fiber
24: cutout
25: step
26, 27: flat portion
30: geared motor
31: gear head
32: pinion
33: (gear head) housing
34: reduction gear mechanism
35: output shaft
36a, 36b, 36c: carrier unit
37, 37c: shaft portion 38: sun gear
39, 39c: carrier
40, 40c: planetary gear
41: internal gear
42: electric power supply wire receiving groove
43: lead wire
46: transparent electrode material
47: PET or glass substrate
48: ITO- or ZnO-based material
49: conductive adhesive or the like
50: protective film
51: reinforcing material
52: adhesive, adhesion tape or the like

BEST MODE FOR CARRYING OUT THE INVENTION

First Embodiment

Figure 2:
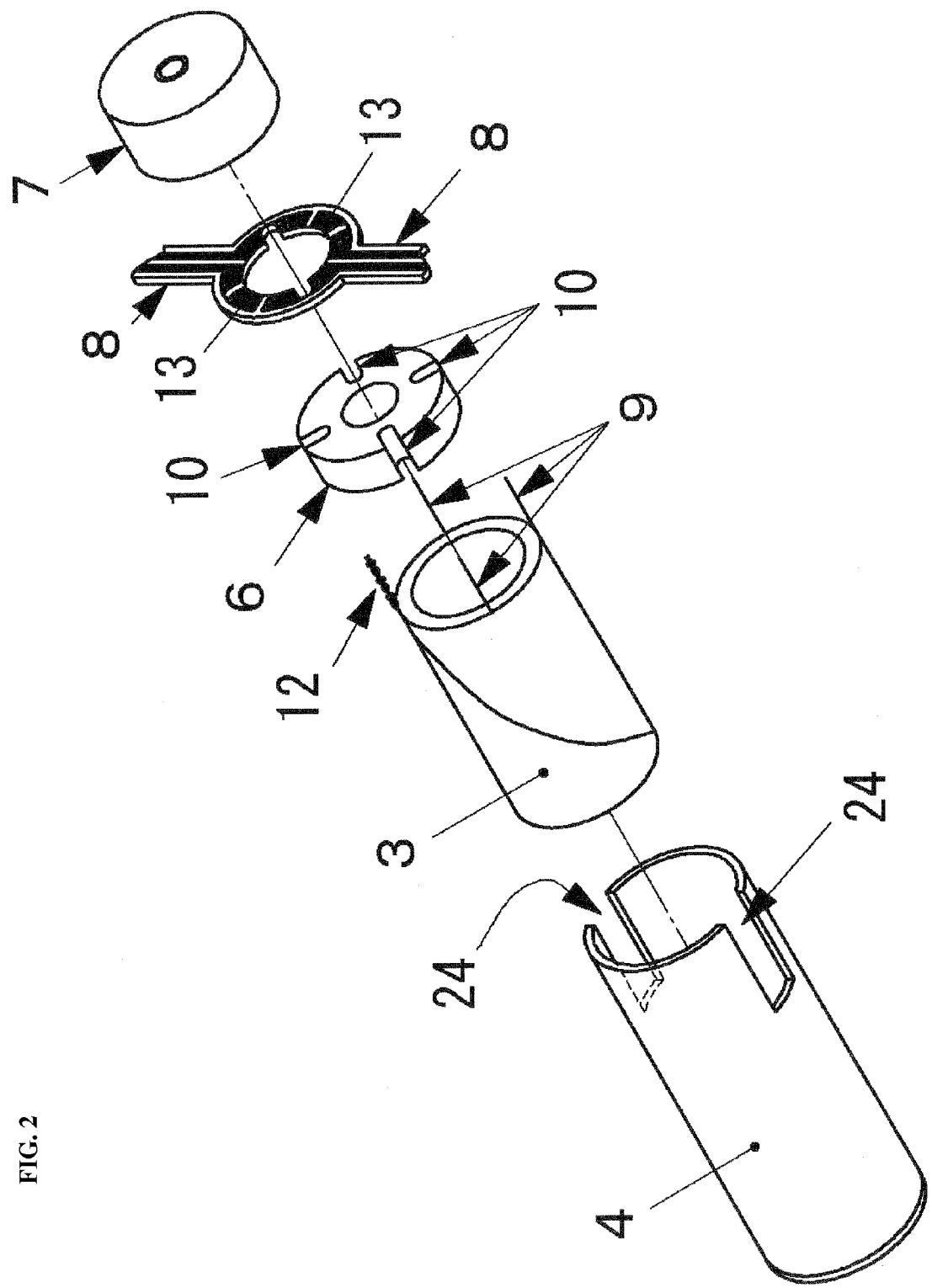
FIG. 2 is an exploded perspective view showing the structure of a stator of the motor of FIG. 1.
Figure 3:
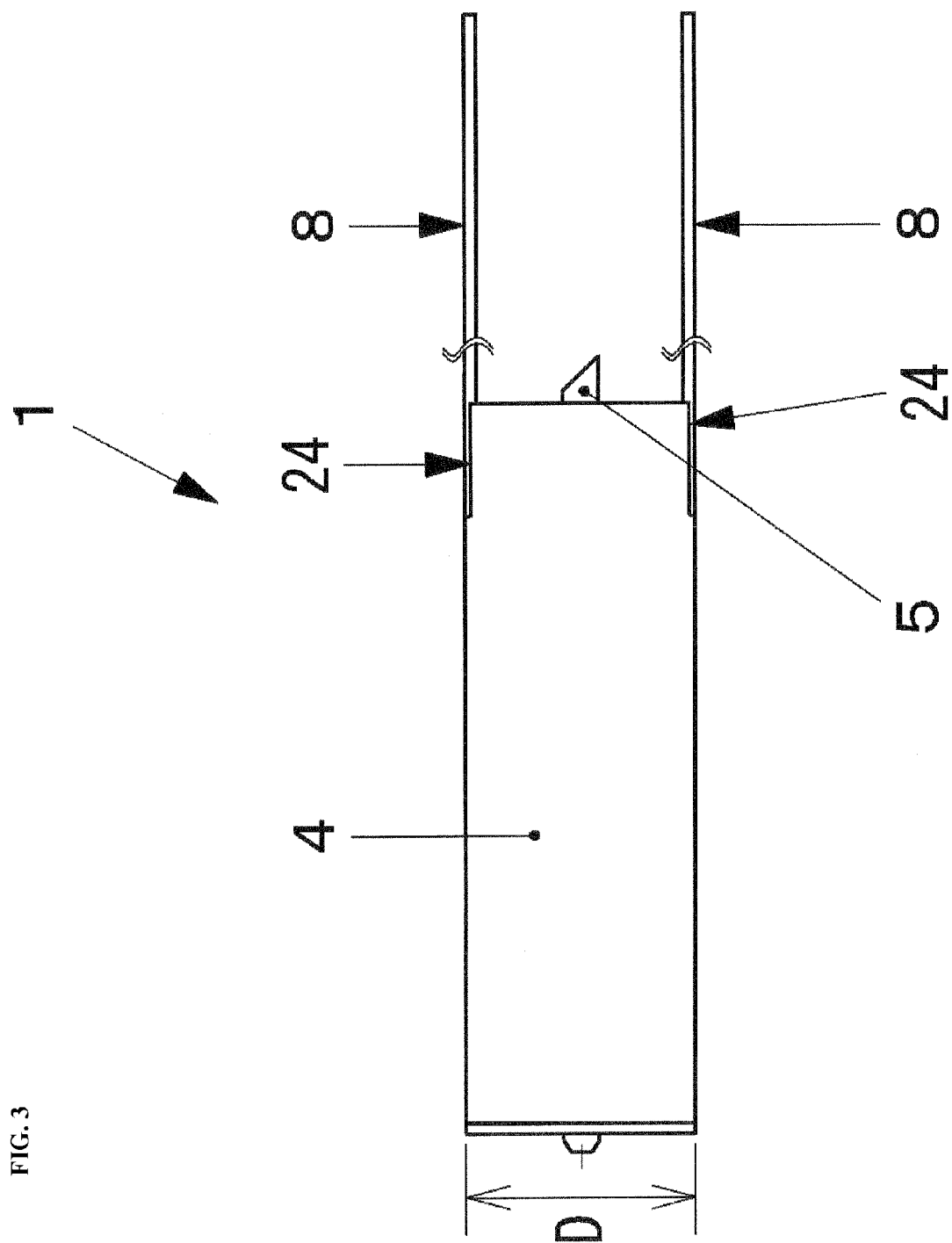
FIG. 3 is a side view of the motor of FIG. 1.
Figure 4:
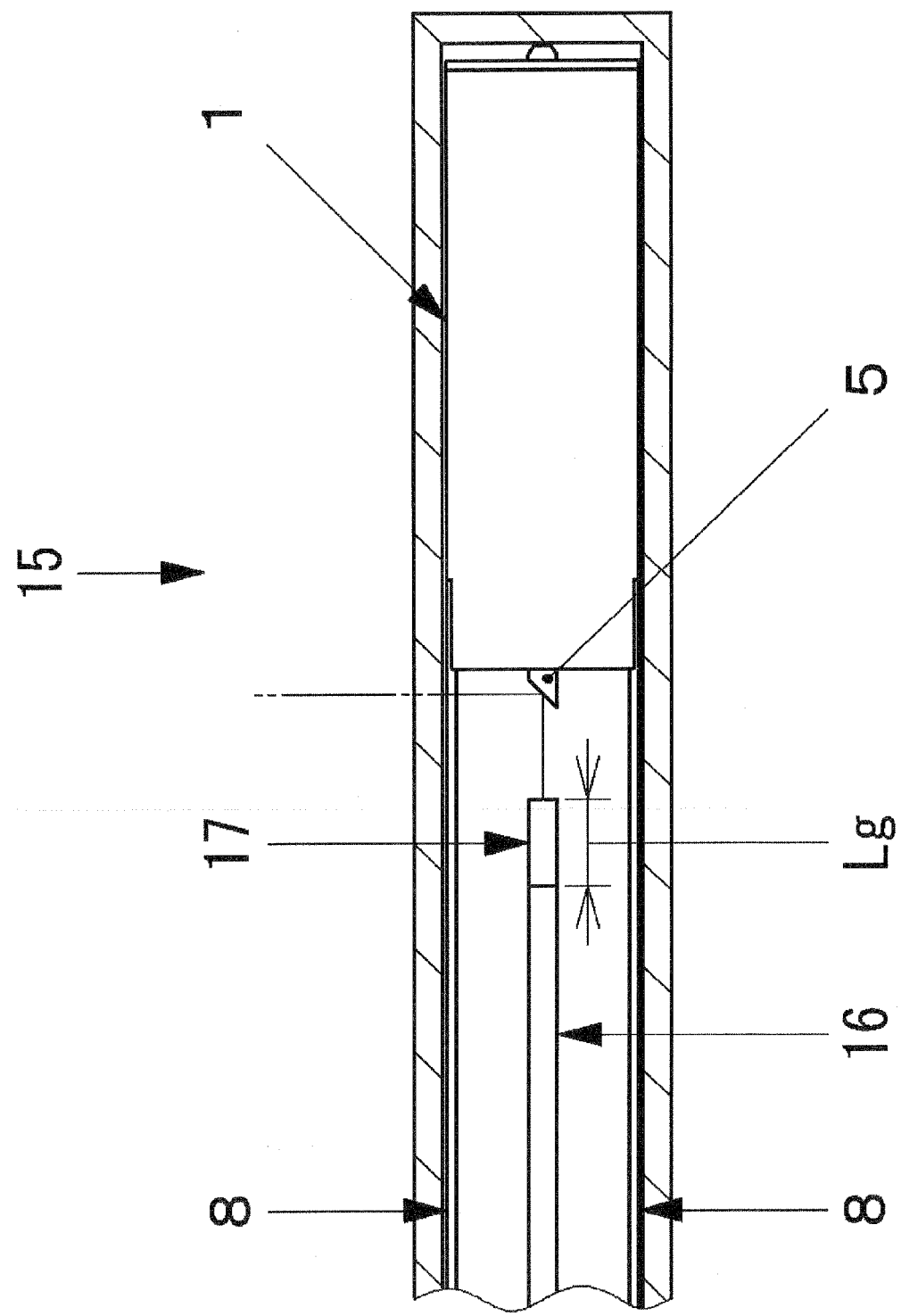
FIG. 4 is a schematic view of the internal structure of an OCT endoscope probe in which the motor of FIG. 1 is mounted.
Figure 5:
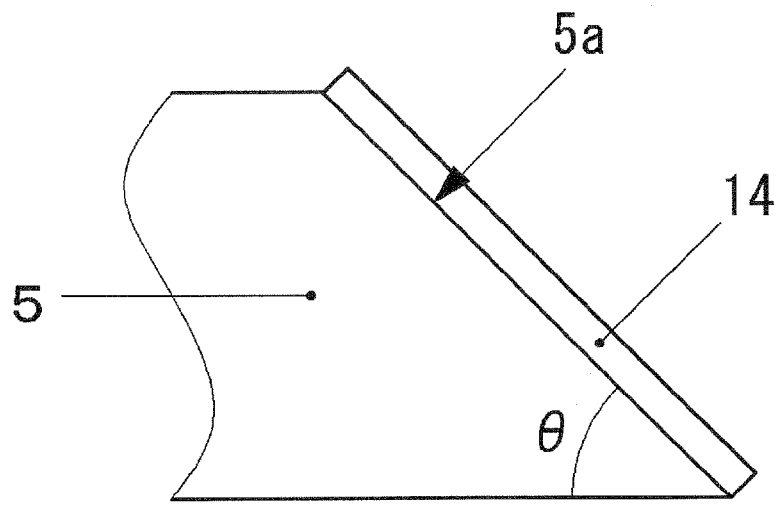
FIG. 5A is a partial enlarged view of an end of a shaft of the motor of FIG. 1 and is a partial enlarged view showing the end of the shaft in which a reflective film is formed on an obliquely formed surface.
FIG. 5B is a partial enlarged view of the end of the shaft of the motor of FIG. 1 and is a partial enlarged view showing the end of the shaft in which the obliquely formed surface is subjected to mirror polishing.
Figure 5:
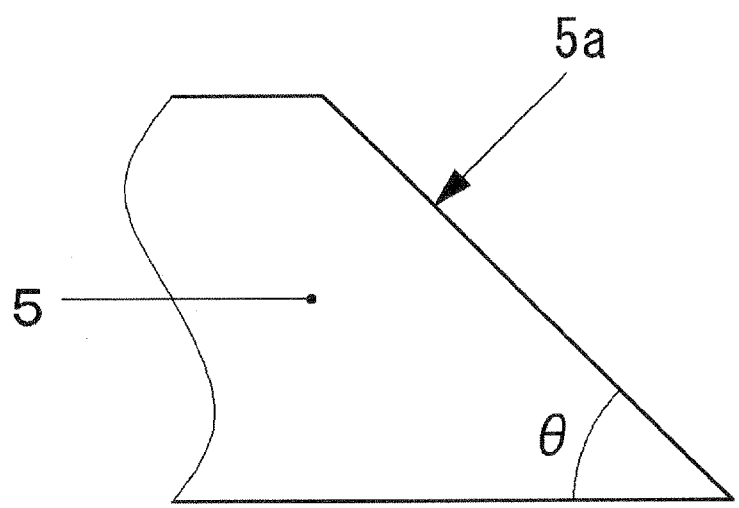

Hereinafter, a first embodiment of a motor and an endoscope probe according to the present invention will be described in detail with reference to FIGS. 1 to 5. FIG. 1 is a cross-sectional view of the motor according to the first embodiment. FIG. 2 is an exploded perspective view showing the structure of a stator of the motor of FIG. 1. FIG. 3 is a side view of the motor of FIG. 1. FIG. 4 is a schematic view of the internal structure of the endoscope in which the motor of FIG. 1 is mounted and, more particularly, an OCT endoscope probe. FIGS. 5A and 5B are partial enlarged views of an end of a shaft of the motor of FIG. 1.

In FIG. 1, the motor 1 includes a magnet 2, a field coil 3, a housing 4, flexible substrates 8 functioning as electric power supply wires, a shaft 5. In FIG. 2, the stator of the motor 1 includes the housing 4, the field coil 3, a lead wire guide 6, a flange 7 and the flexible substrates 8.

The appearance of the housing 4 has a substantially cylindrical shape and cutouts 24 and 24 are formed in an end thereof. Six lead wires are lead out from the field coil 3, and a total of three tap wires 9 and twisted wires 12 which are neutral points are formed one by one. Four grooves 10 are included in the lead wire guide 6. The flange 7 includes shaft bearings 11 (see FIG. 1).

Meanwhile, as shown in FIG. 1, the field coil 3 is placed on and fixed to an inner wall of the housing 4, and the lead wire guide 6 is placed on the side of the tap wires 9 and the twisted wires 12 of the field coil 3. A rotor including the magnet 2 and the shaft 5 penetrating through the center thereof is inserted into the field coil 3 so as to face the inside of the field coil 3 with a gap interposed therebetween and is rotatably held by the shaft bearings 11 and 11. Accordingly, the magnet 2 and the shaft 5 are placed in the housing 4.

The tap wires 9 and the twisted wires 12 formed by leading out from the field coil 3 are extended in the grooves 10 of the lead wire guide 6 and connected to the flexible substrates 8 and 8. At this time, by adhering electric power supply lands 13 of the flexible substrates 8 and 8, portions in which the tap wires 9 and the twisted wires 12 are connected by a solder and the grooves 10 with an adhesive or the like, a structure, in which disconnection is prevented without exerting overload on the tap wires 9, the twisted wires 12 and connection portions, is obtained, and fixing strength is increased. The field coil 3, the lead wire guide 6 and the flexible substrate 8 and 8 are received in the housing 4, and the flange 7 is inserted into and fixed to the end side of the housing 4 in which the cutouts 24 and 24 are formed. Since the flange 7 is inserted into the end side of the housing 4, the outer diameter of the flange 7 is equal to or less than that of the housing 4. By the above-described configuration, a DC brushless motor 1 is formed and the overall outer diameter D of the motor 1 (see FIG. 3) may be set to about 2 mm which is equal to or less than 3 mm.

The flexible substrates 8 and 8, to which the lead wires (the tap wires 9 and twisted wires 12) are connected, are bent at a right angle and received along the cutouts 24 and 24 so as to be led out to the outside of the motor 1 without protruding from the outer diameter of the motor 1. The direction in which the flexible substrates 8 and 8 are led out is equal to the direction in which the shaft 5 projects.

In the motor 1 according to the present invention, as shown in FIGS. 3 and 5, the end of the shaft 5 is obliquely cut to the axial direction of the shaft 5 such that the end of the shaft 5 is obliquely formed in the axial direction of the shaft 5. The cut angle θ may be set to a desired angle according to the requirement characteristics of the endoscope probe in which the motor 1 is mounted. In the present embodiment, the cut angle is, for example, 45 degrees. In addition, stainless steel is generally used in the shaft 5.

In an obliquely formed surface 5a of the shaft 5, a reflective film 14 is formed (see FIG. 5A) or mirror polishing is performed (see FIG. 5B) such that a light reflection surface is formed. If the mirror polishing is performed, the obliquely formed surface 5a is mechanically polished so as to perform mirror finishing. In addition, if the reflective film 14 is formed, a metallic film or a dielectric multi-layer film with high reflectivity, such as aluminum, nickel, gold or silver, is formed on the obliquely formed surface 5a. As the film forming method, deposition, sputtering, CVD, plating, coating or the like may be used.

Alternatively, the overall shaft 5 may be formed of amorphous metal alloy. By such a configuration, the reflection surface is formed of the amorphous metal alloy, but the surface roughness Ry of the reflection surface is set to 0.4 μm or less and more preferably 0.1 μm or less. By setting the surface roughness Ry to the above range, it is possible to prevent light reflection efficiency of the reflection surface from deteriorating.

As the amorphous metal alloy, amorphous metal alloy having at least one of elements such as Fe, Ni, Cu, Ti and Zr as main components is preferably used.

If the overall shaft 5 is formed of amorphous metal alloy, the overall shaft 5 is manufactured by injection molding. In particular, it is preferable that polishing is performed to a mold for molding the reflection surface and the mold surface roughness Ry is set to 0.4 μm or less and, more particularly, 0.1 μm or less, because the light reflection efficiency of the reflection surface after transferring is prevented from deteriorating as described above.

Alternatively, the light reflection surface may be formed in the obliquely formed surface 5a by combining the technical elements, for example, mirror-polishing the obliquely formed surface 5a of the shaft 5 and forming the reflective film 14 on the obliquely formed surface 5a. In addition, the light reflection surface may be formed in the obliquely formed surface 5a by forming the overall shaft 5 using amorphous metal alloy, setting the surface roughness Ry of the obliquely formed surface 5a of the shaft 5 to 0.4 μm or less and forming the reflective film 14 on the obliquely formed surface 5a.

The motor 1 configured as described above is mounted in the OCT endoscope probe 15 shown in FIG. 4 (hereinafter, referred to as the probe 15 if necessary). In the OCT endoscope probe 15, a single mode optical fiber 16 is provided as an optical propagation path, and the motor 1 is further placed on a distal portion in the body of the OCT endoscope probe 15. When the motor 1 is placed in the body of the OCT endoscope probe 15, the direction in which the shaft 5 projects to the outside of the motor 1 is opposite to the direction of the front end of the OCT endoscope probe 15. By placing the motor 1 as described above, the reflection surface of the end of the shaft 5 faces the end of the optical fiber 16.

On the end of the optical fiber 16, in order to collimate the light emitted from the optical fiber 16 or make the light convergent so as to set a focal point, a graded-index optical fiber 17 is included. The reflection surface faces the end of the graded-index optical fiber 17 such that the light emitted from a light source (not shown) is propagated in a core of the optical fiber 16, is emitted from the end of the graded-index optical fiber 17, and is reflected from the reflection surface, the optical path thereof is changed by 90 degrees, and the light is irradiated to an organ, thereby forming an image. In addition, the reflection surface is rotated by driving the motor 1 so as to perform OCT scanning such that tomogram of an organ wall is acquired.

Figure 24:
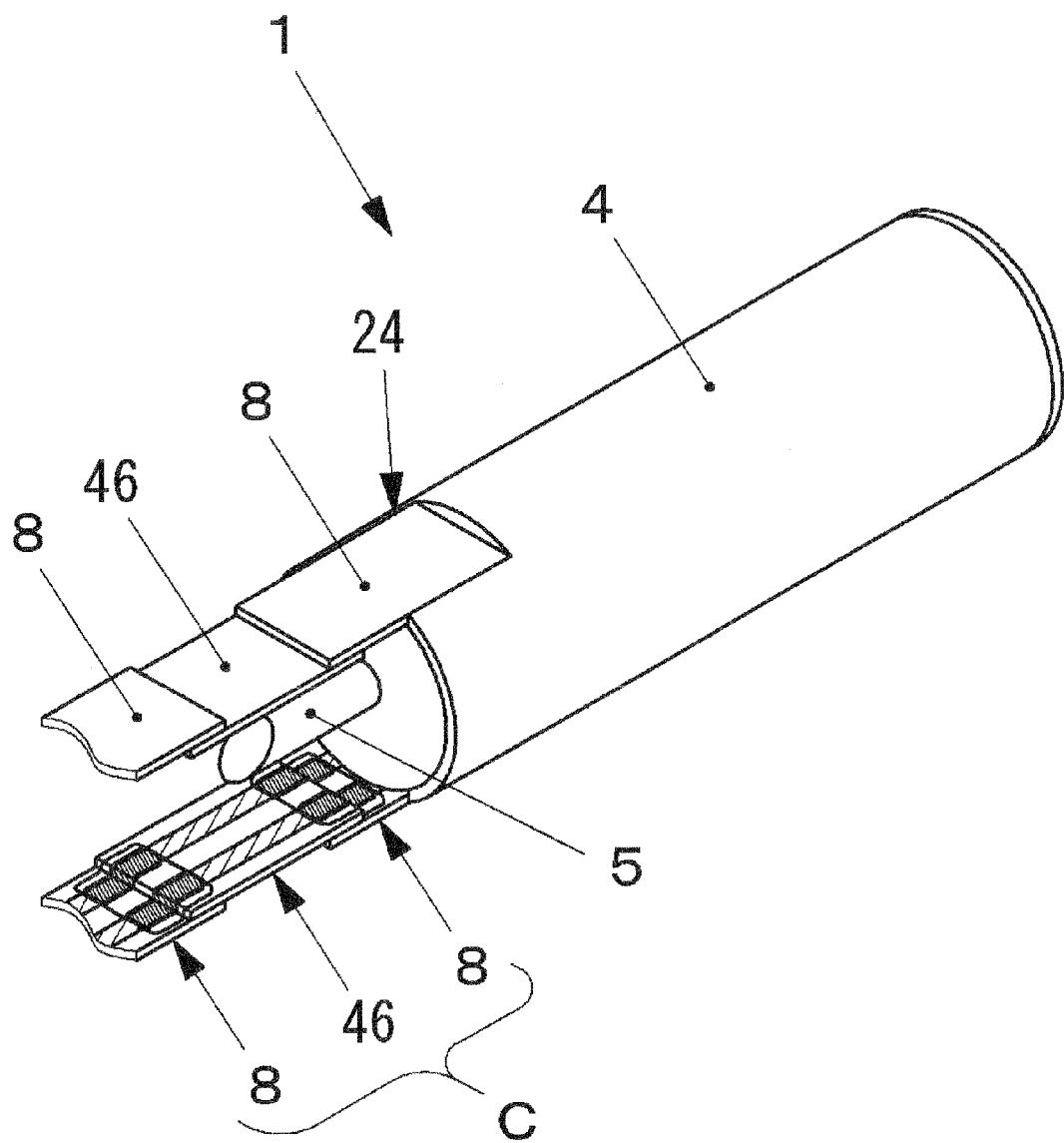
FIG. 24 is a perspective view of a motor according to the present invention in which a portion of the electric power supply wire is formed of a transparent electrode material.
Figure 25:
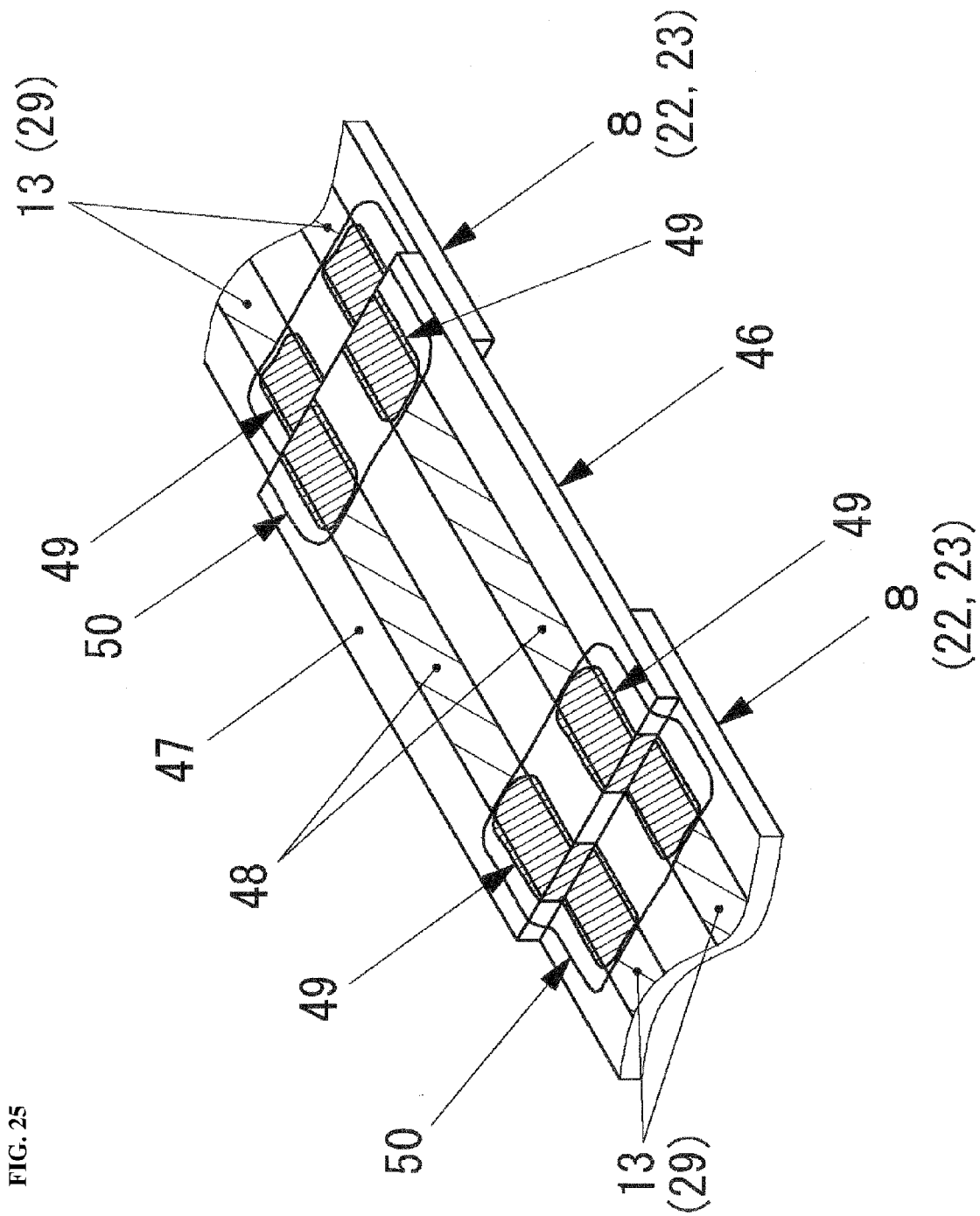
FIG. 25 is an enlarged perspective view of an electric power supply wire portion C of FIG. 24.
Figure 26:
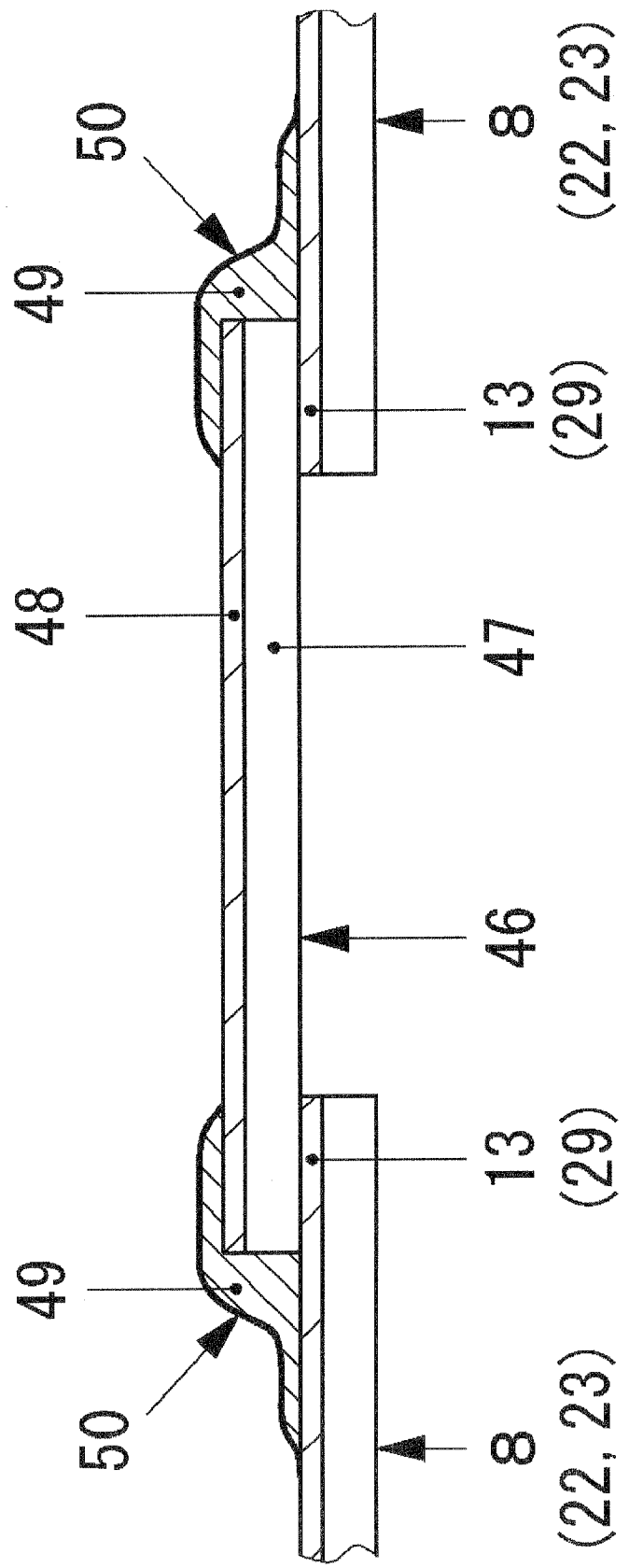
FIG. 26 is a side view schematically showing FIG. 25.

In addition, as shown in FIGS. 24 and 25, at least a portion or whole of the two flexible substrates 8 and 8 may be changed to be formed of a transparent electrode material 46 which is optically transparent. FIG. 25 is an enlarged view of an electric power supply wire portion C formed of the transparent electrode material 46 and the flexible substrates 8 and 8 of FIG. 24. As shown in FIGS. 25 and 26, as the transparent electrode material 46, an Indium Tin Oxide (ITO) 48 patterned on a Polyethylene Terephthalate (PET) surface 47 or a ZnO-based material 48 patterned on the surface of the PET 47 or a glass substrate 47 is suitably used. The electrical connection between the electric power supply lands 13 of the flexible substrates 8 and 8 and the transparent electrode (ITO- or ZnO-based material) 48 is, as shown in FIGS. 25 and 26, performed by compression bonding or a conductive adhesive, a low melting point solder, or various pastes such as a silver paste, a copper paste or a carbon paste denoted by a reference numeral 49, and a connection portion is covered by a protective film 50.

Figure 27:
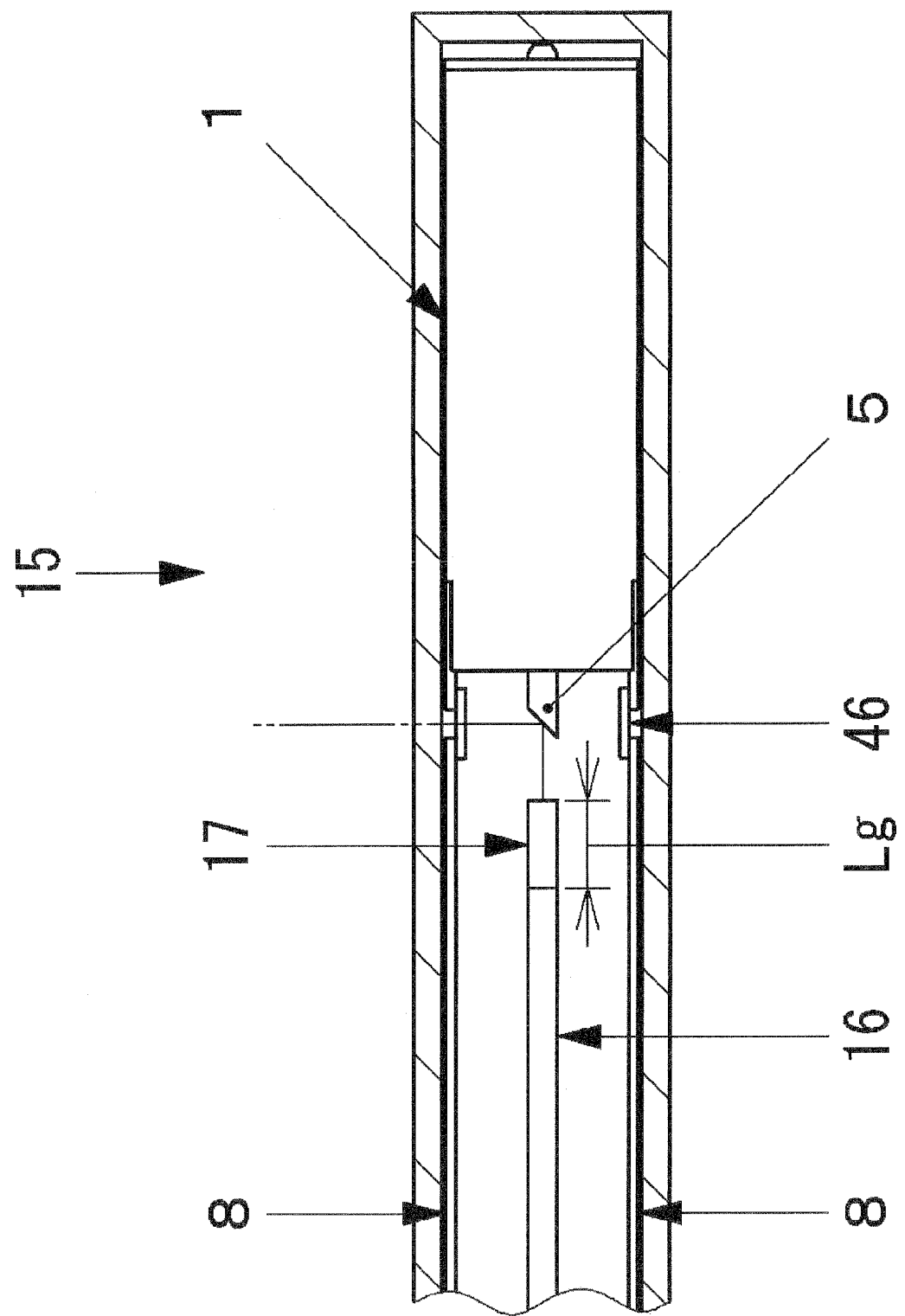
FIG. 27 is a schematic view of the internal structure of an OCT endoscope probe in which the motor of FIG. 24 is mounted.
Figure 28:
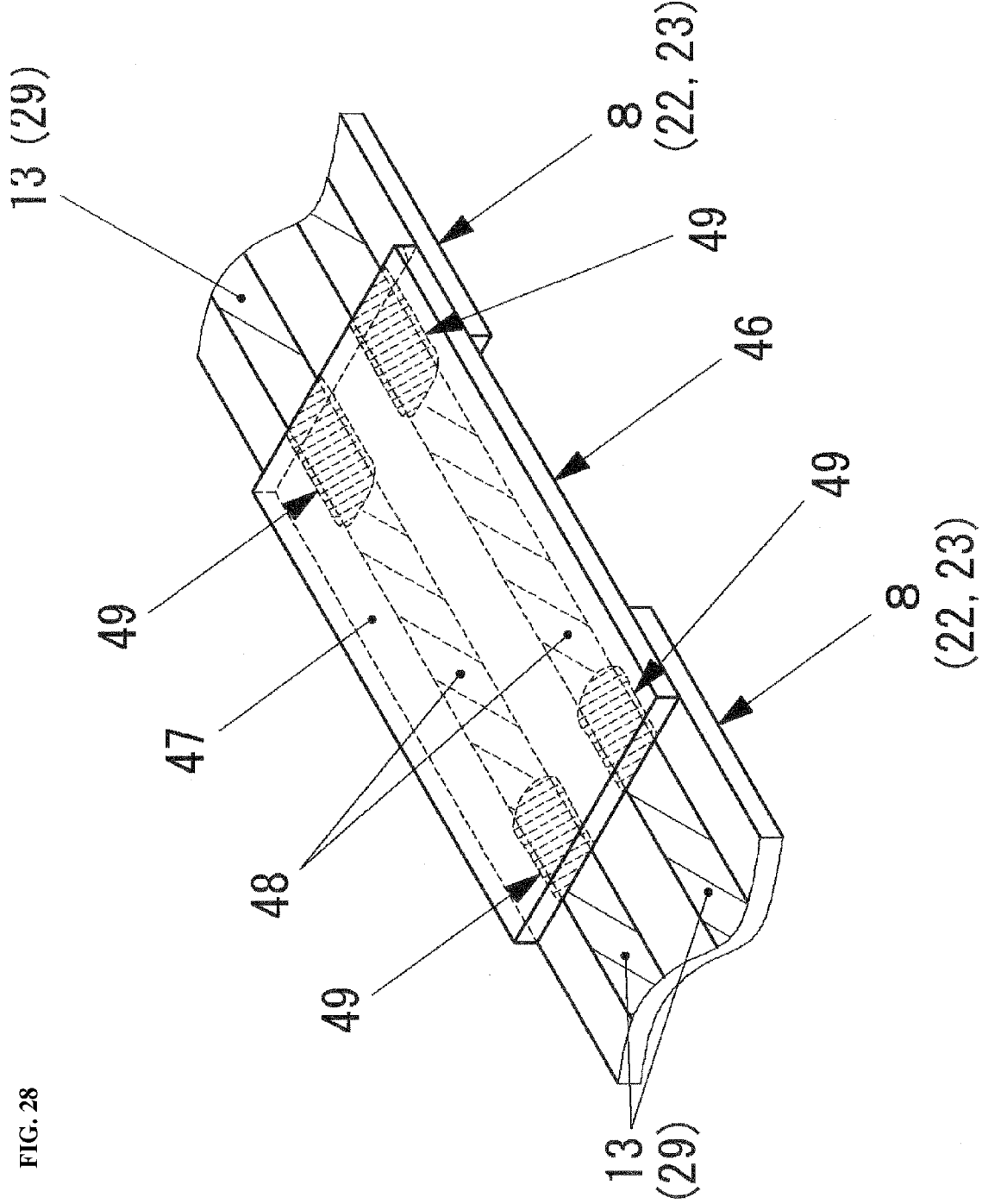
FIG. 28 is an enlarged perspective view showing a modified example of FIG. 25.
Figure 29:
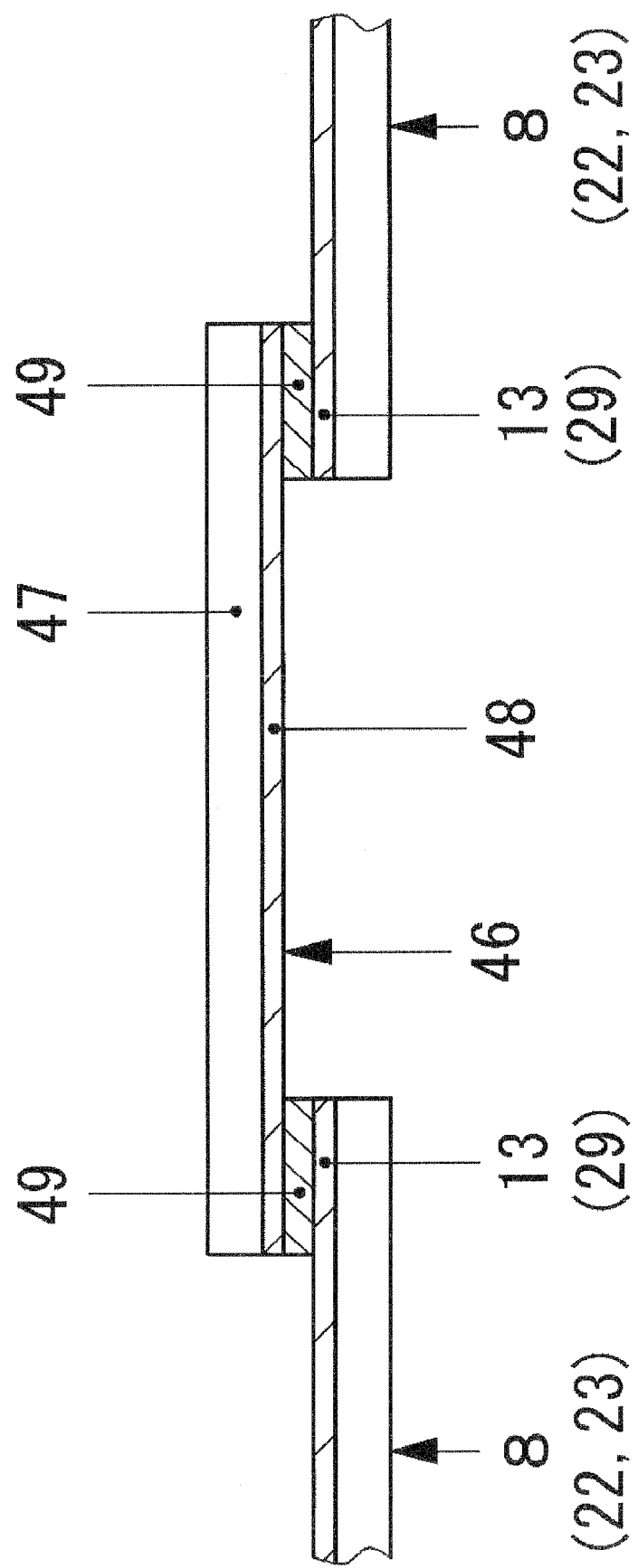
FIG. 29 is a side view schematically showing FIG. 28.
Figure 30:
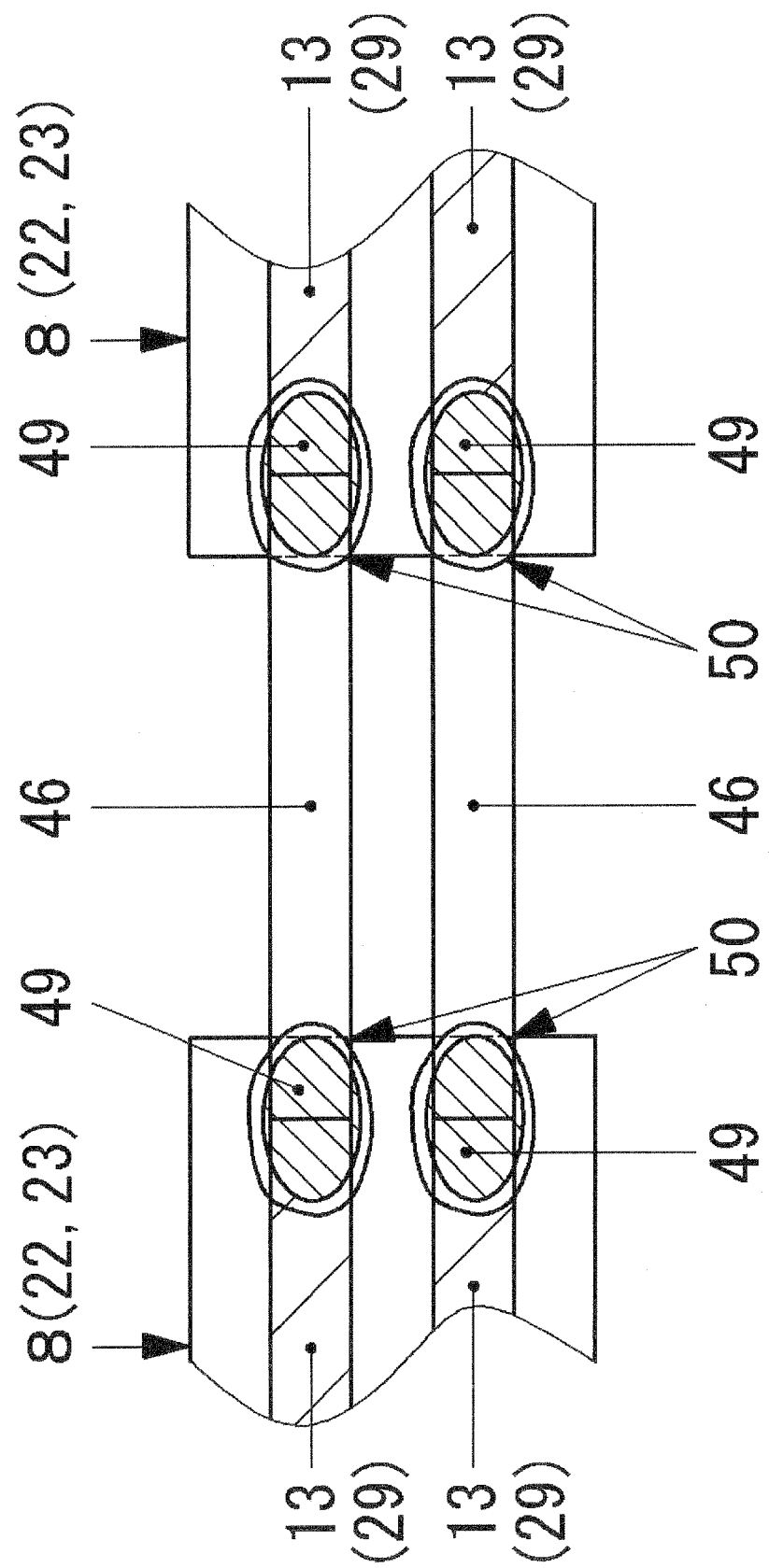
FIG. 30 is a partial plan view showing another modified example of FIG. 25.

The portion of the flexible substrates 8 and 8 is the electric power supply wire portion placed on the optical path of the light reflected from the reflection surface of the shaft 5 which is a portion of the motor 1. Accordingly, at the time of scanning of the probe 15, as shown in FIG. 27, the portion of the transparent electrode material 46 which does not overlap with the flexible substrates 8 and 8 is placed on the optical path of the reflected light. By forming at least a portion of the electric power supply wires (flexible substrates 8) using the transparent electrode material 46, it is possible to prevent the electric power supply wires from becoming an obstacle at the time of 360-degree scanning of the probe 15. As described above, the flexible substrates 8 may be replaced with a lead wire or a leaf spring type connection terminal. In addition, the electrical connection between the electric power supply lands 13 and the transparent electrode (ITO- or ZnO-based material) 48 may be performed by, as shown in FIGS. 28 and 29, facing the electric power supply lands 13 and the transparent electrode (ITO- or ZnO-based material) 48 or by, as shown in FIG. 30, electrically connecting only the electric power supply lands 13 and 13 of the flexible substrates 8 and 8 to the transparent electrode material 46.

Figure 31:
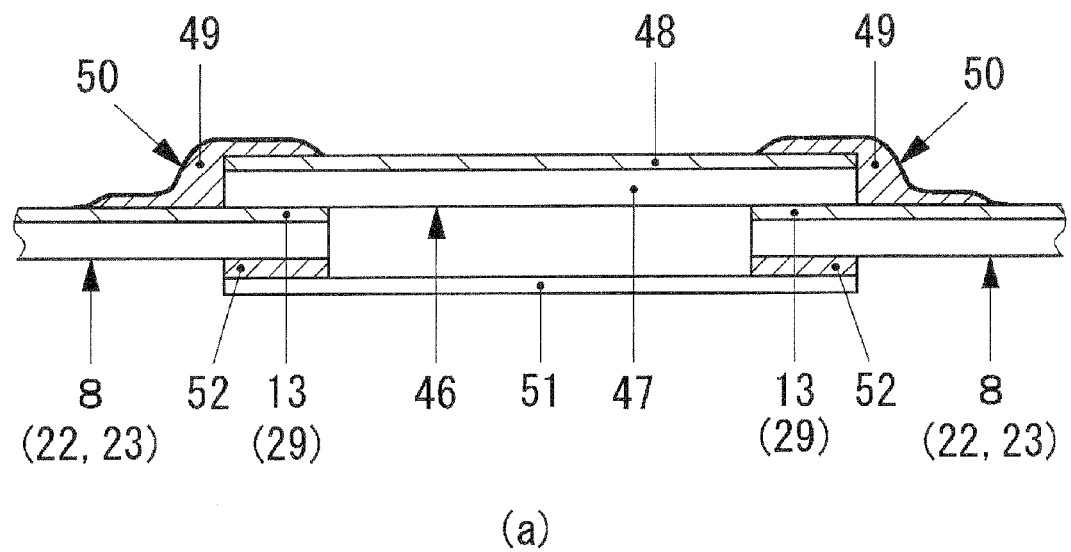
FIG. 31A is a side view showing a structure in which a reinforcing material is used in the electric power supply wire portion of FIG. 26.
FIG. 31B is a side view showing a structure in which a reinforcing material is used in the electric power supply wire portion of FIG. 29.
Figure 31:
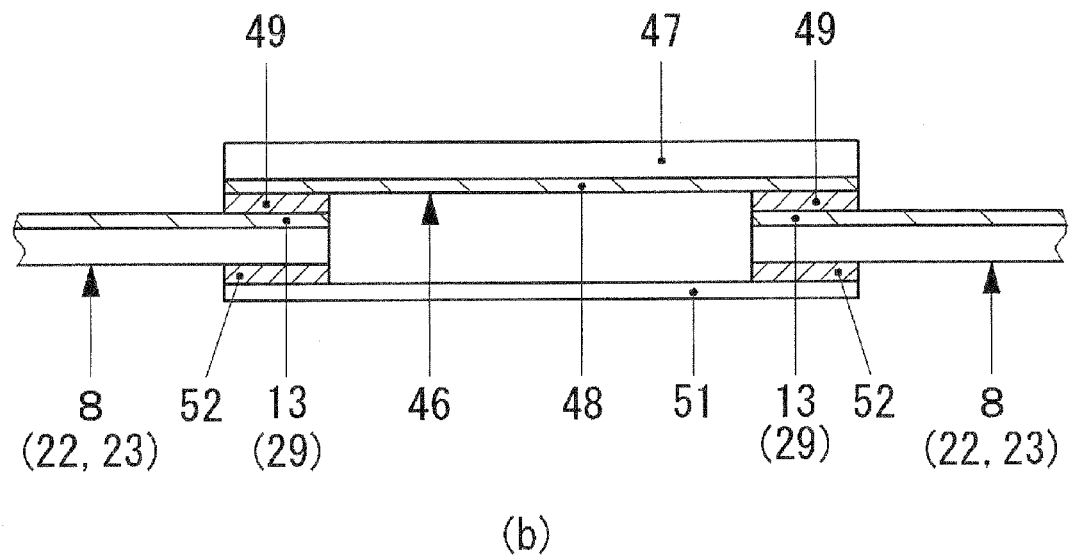

As shown in FIG. 31A or 31B, a high transmissivity material in a wavelength region of the light propagating in the optical fiber 16 may be used as a reinforcing material 51 of the connection portion of the transparent electrode material 46. The fixing of the reinforcing material 51 may be performed by an adhesive, an adhesion tape or the like, which is denoted by a reference numeral 52.

The graded-index optical fiber 17 includes a clad and a core having a gradient having a parabolic refractive distribution. The length Lg of the graded-index optical fiber is set to a length corresponding to a quarter of a zigzag period of the light propagating in the core or an odd multiple thereof, when it is used for collimation. In contrast, if the graded-index optical fiber is used for light convergence, the length thereof is set to a quarter to a half of the zigzag period of the light propagating in the core.

If the graded-index optical fiber 17 is formed, the graded-index optical fiber 17 may be fusion-spliced to one end of the optical fiber 16 and, thereafter, the graded-index optical fiber 17 may be cut with a desired core length Lg.

Alternatively, the graded-index optical fiber 17 may be replaced with a GRIN lens. If the GRIN lens is used for collimation, the length (corresponding to Lg) of the GRIN lens may be set to 0.25P (P: the pitch of the GRIN lens) or an odd multiple of 0.25P. In contrast, if the GRIN lens is used for light convergence, the length (corresponding to Lg) of the GRIN lens may be set to a range from 0.25P to 0.5P.

As described above, the flexible substrates 8 and 8 are received along the cutouts 24 and 24 so as to be led out to the outside of the motor 1 without protruding from the outer diameter of the motor 1. Accordingly, when the motor 1 is mounted in the body of the OCT endoscope probe 15, the flexible substrates 8 and 8 are routed along the longitudinal direction of the OCT endoscope probe 15. Accordingly, when the flexible substrates 8 and 8 are routed in the body of the probe 15, the flexible substrates 8 and 8 may not be bent. Accordingly, it is possible to prevent disconnection of the flexible substrates 8 and 8 and to solve generation of R (corner R) of a bent portion generated due to bending. Therefore, it is possible to suppress the increase in diameter of the probe 15 and to shorten an inflexible portion of the front end of the probe 15.

In addition, since the flexible substrates 8 and 8 are received in the cutouts 24 and 24 and are led out to the outside of the motor 1, it is possible to prevent protrusion of the electric power supply wires (flexible substrates 8 and 8) in the diameter direction of the motor 1. Even in this case, it is possible to suppress the increase in diameter of the probe 15.

In the electric power supply wire, instead of the flexible substrates 8 and 8, for example, a lead wire or a leaf spring type connection terminal may be used. In addition, the connection between the lead wire of the field coil 3 and the electric power supply wires may be performed by a connection terminal, instead of direct fixing using a solder, in the present embodiment.

As described above, according to the present embodiment, since the end of the shaft 5 of the motor 1 is formed by the light reflection surface, an optical part for a scanner, such as a mirror or a prism, is unnecessary in the end of the shaft 5. Accordingly, a space occupied by the scanner in the internal space of the front end of the probe can be eliminated and the inflexible portion of the front end of the OCT endoscope probe 15 can be shortened. In addition, the number of parts can be reduced.

Since the light reflection surface is directly formed in the end of the shaft 5, the optical path of the light after being reflected from the reflection surface can be set by desire and efficient light transmission to the subject can be achieved.

In addition, since a separate part such as the optical part for the scanner is not attached to the shaft 5 of the motor 1, it is possible to rotate the shaft 5 with low torque and suppress the increase in size of the motor 1. Accordingly, it is possible to suppress the increase in diameter of the overall OCT endoscope probe 15.

By removing the optical part for the scanner, it is possible to reduce one axial shift element between the core axis of the optical fiber 16 and axis of the motor 1.

By forming the reflective film 14 on the end of the shaft 5 or performing mirror polishing, the light reflection efficiency of the end of the shaft 5 is improved and thus light propagation efficiency is also improved.

Since the amorphous metal alloy does not have a crystal grain boundary, it is possible to improve surface smoothness of the reflection surface by forming the overall shaft 5 using the amorphous metal alloy. Accordingly, since the amorphous metal alloy has a good mold transfer property in the injection molding process or a good polishing property in the polishing process, surface smoothness is excellent. As a result, the reflection efficiency of the manufactured reflection surface is also improved and the light propagation efficiency is also improved.

In addition, by mirror-polishing the obliquely formed surface 5a of the shaft 5 and forming the reflective film 14 on the obliquely formed surface 5a so as to form the light reflection surface on the obliquely formed surface 5a or by forming the overall shaft 5 using the amorphous metal alloy, setting the surface roughness Ry of the obliquely formed surface 5a of the shaft 5 to 0.4 μm or less and forming the reflective film 14 on the obliquely formed surface 5a so as to form the light reflection surface on the obliquely formed surface 5a, the obliquely formed surface 5a on which the reflective film 14 is formed is mirror-formed and the reflective film 14 is then formed. Accordingly, it is possible to further improve the reflection efficiency of the reflection surface.

The probe 15 may be an ultrasonic probe or other probe, instead of the OCT probe. When the motor 1 is placed in the ultrasonic endoscope probe body, the direction in which the shaft 5 projects to the outside of the motor 1 is opposite to the direction of the front end of the ultrasonic endoscope probe, such that the reflection surface of the end of the shaft 5 faces an ultrasonic vibrator. The ultrasonic waves radiated from the ultrasonic vibrator are reflected from the reflection surface, and the reflection surface is rotated and driven by the motor 1, thereby performing scanning.

Even when the motor 1 is mounted in the ultrasonic endoscope probe, similar to the OCT endoscope probe, the electric power supply wires (flexible substrates 8 and 8) are routed along the longitudinal direction of the ultrasonic endoscope probe. Accordingly, when the electric power supply wires are routed in the ultrasonic endoscope probe body, the electric power supply wires may not be bent. Therefore, it is possible to prevent disconnection of the electric power supply wires and to solve generation of R (corner R) of the bent portion generated due to bending. Accordingly, it is possible to suppress the increase in diameter of the ultrasonic endoscope probe and to shorten an inflexible portion of the front end of the ultrasonic endoscope probe. In addition, since the flexible substrates 8 and 8 are received in the cutouts 24 and 24 and are led out to the outside of the motor 1, it is possible to prevent protrusion of the electric power supply wires (flexible substrates 8 and 8) in the diameter direction of the motor 1. Even in this case, it is possible to suppress the increase in diameter of the probe 15.

Instead of that the reflection surface is not formed on the end of the shaft 5, a motor in which the ultrasonic vibrator is fixed may be changed to be placed in the ultrasonic endoscope probe body. Even when such a motor is placed, the direction in which the shaft projects to the outside of the motor is opposite to the direction of the front end of the ultrasonic endoscope probe, such that the bending of the electric power supply wires is prevented when the electric power supply wires is routed. In addition, since the flexible substrates 8 and 8 are received in the cutouts 24 and 24 and are led out to the outside of the motor 1, it is possible to prevent protrusion of the electric power supply (flexible substrates 8 and 8) in the diameter direction of the motor 1. Even in this case, it is possible to suppress the increase in diameter of the ultrasonic endoscope probe.

Second Embodiment

Figure 6:
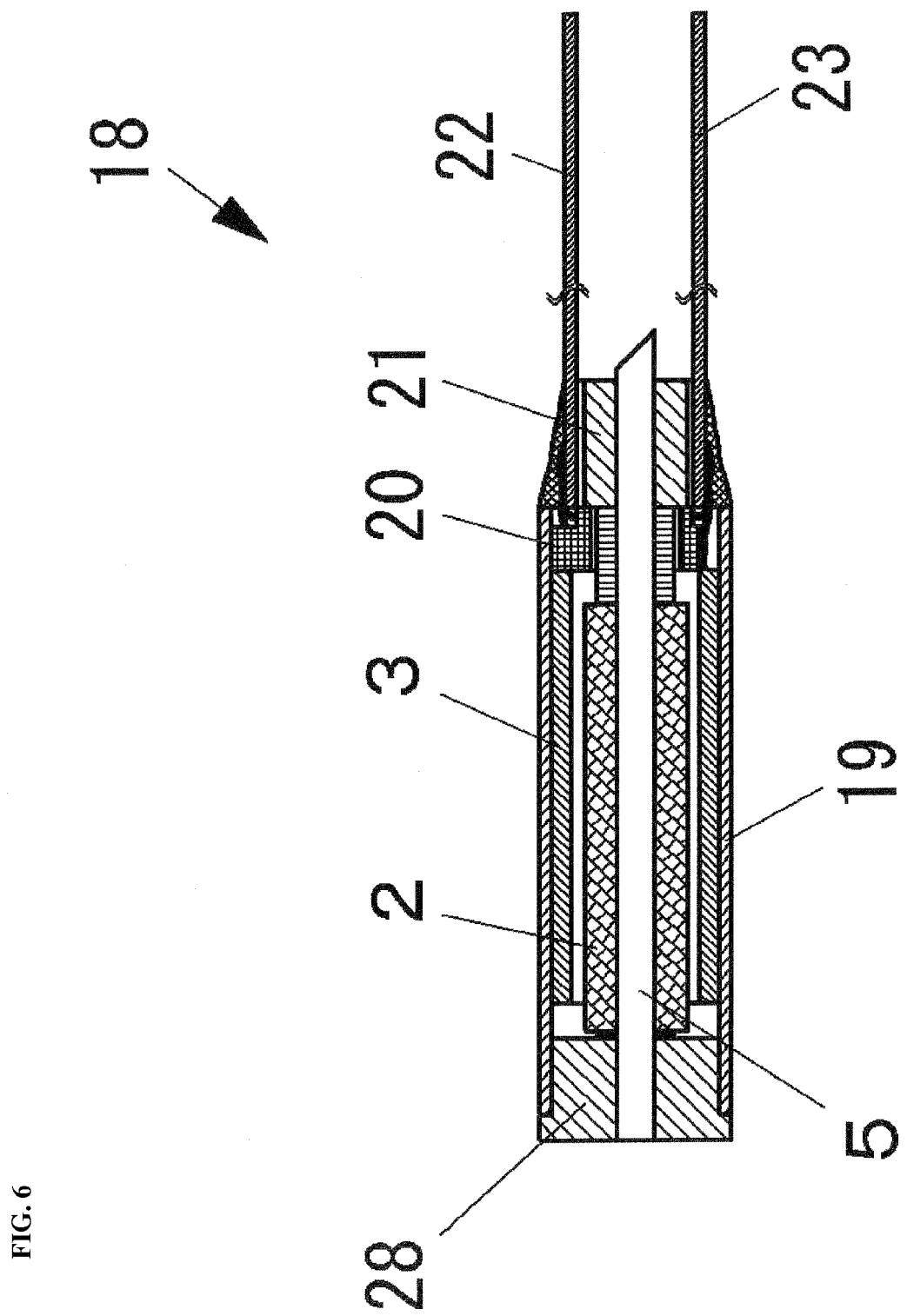
FIG. 6 is a cross-sectional view of a motor according to a second embodiment of the present invention.
Figure 7:
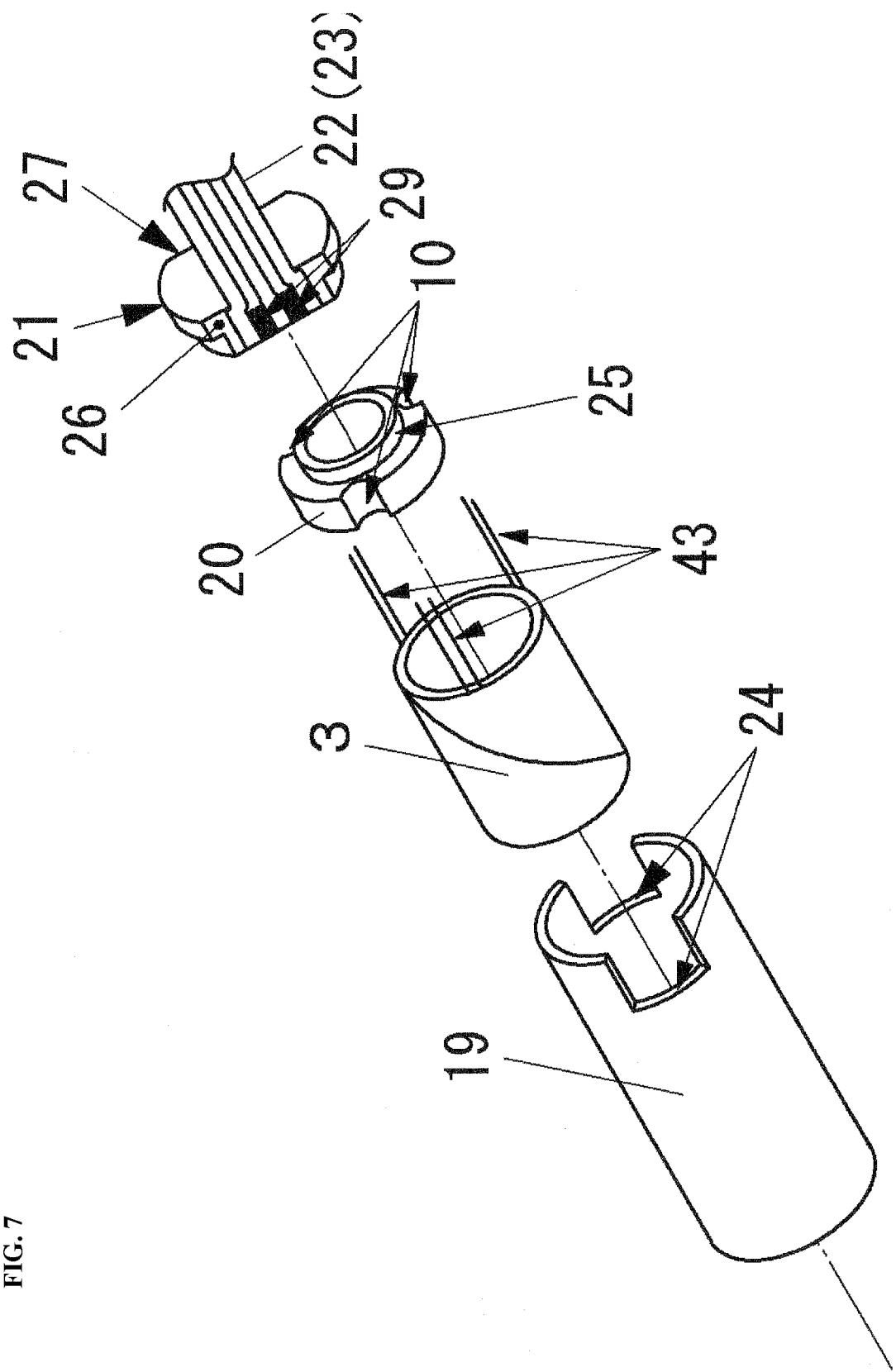
FIG. 7 is an exploded perspective view showing the structure of a stator of the motor of FIG. 6.
Figure 8:
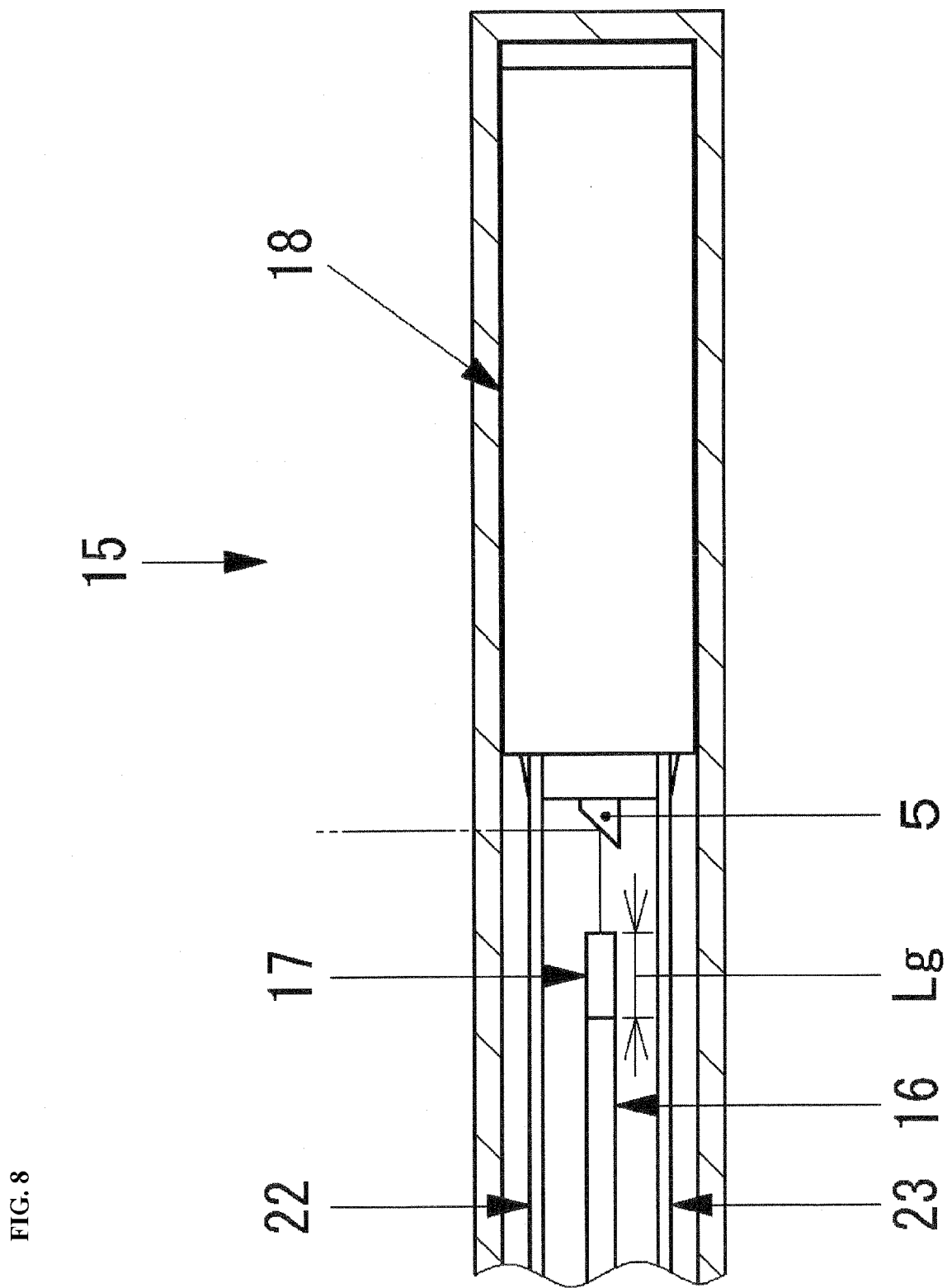
FIG. 8 is a schematic view of the internal structure of an OCT endoscope probe in which the motor of FIG. 6 is mounted.

Hereinafter, a second embodiment of a motor and an OCT endoscope probe according to the present invention will be described in detail with reference to FIGS. 6 to 8. FIG. 6 is a cross-sectional view of the motor according to the second embodiment. FIG. 7 is an exploded perspective view showing the structure of a stator of the motor of FIG. 6. FIG. 8 is a schematic view of the internal structure of the endoscope probe in which the motor of FIG. 6 is mounted and, more particularly, the OCT endoscope probe. In the description of the motor 18 according to the second embodiment, the portions overlapping with those of the motor 1 are denoted by the same reference numerals and the description thereof will be omitted or simplified. The stator of the motor 18 includes a housing 19, a field coil 3, a lead wire guide 20, a flange 21 and flexible substrates 22 and 23.

The appearance of the housing 19 has a substantially cylindrical shape and cutouts 24 and 24 are formed in an end thereof. Six lead wires 43 are lead out from the field coil 3. A step 25 and three grooves 10 are formed in the lead wire guide 20. In addition, the flange 21 inserted into and fixed to the end of the housing 19 also functions as the shaft bearing, and flat portions 26 and 27 are included in the outer circumferential surface thereof. In addition, the flexible substrates 22 and 23 are placed on and fixed to the flat portions 26 and 27 with the same configuration. A flange 28 is inserted into and fixed to another end of the housing 19, to which the flange 21 is fixed, and the flange 28 also functions as a shaft bearing.

As shown in FIG. 6, the field coil 3 is fixed to the inner wall of the housing 19, and the lead wire guide 20 is placed on the side of the lead wires 43 of the field coil 3. A rotor including a magnet 2 and a the shaft 5 penetrating through the center thereof is inserted into the field coil 3 with a gap interposed therebetween and is rotatably held by the flange 28 and the flange 21.

In addition, the lead wires 43 are led out and routed in a space formed by the step 25 and the grooves 10 of the lead wire guide 20, and a total of three tap wires and twisted wires which are neutral points are formed one by one. The tap wires and the twisted wires are connected to the flexible substrates 22 and 23 by a solder such that the lead wires 43 are connected to the outer circumferential surface of the motor 18.

At this time, by filling the grooves 10 and the step 25 with an adhesive or the like, and adhering electric power supply lands 29 of the flexible substrates 22 and 23 and portions, in which the tap wires and the twisted wires are connected with a solder, with an adhesive or the like, a structure, in which disconnection is prevented without exerting overload on the tap wires and connection portions, is obtained, and fixing strength is increased. The field coil 3 and the lead wire guide 20 are received in the housing 19, the flange 21 is inserted into and fixed to the end of the housing 19 while aligning the flat portions 26 and 27 at the positions of the cutouts 24 and 24, and the flexible substrates 22 and 23 are received along the cutouts 24 and 24.

The flexible substrates 22 and 23, to which the lead wires 43 (the tap wires and twisted wires) are connected, are received along the cutouts 24 and 24 so as to be led out to the outside of the motor 18 without protruding from the outer diameter of the motor 18. The direction in which the flexible substrates 22 and 23 are led out is equal to the direction in which the shaft 5 projects.

The motor 18 configured as described above is mounted in the OCT endoscope probe 15 shown in FIG. 8.

The motor 18 is placed on a distal portion in the body of the OCT endoscope probe 15. When the motor 18 is placed in the body of the OCT endoscope probe 15, the direction in which the shaft 5 projects to the outside of the motor 18 is opposite to the direction of the front end of the OCT endoscope probe 15. By placing the motor 18 as described above, the reflection surface of the end of the shaft 5 faces the end of the optical fiber 16.

The light emitted from a light source (not shown) is propagated in the core of the optical fiber 16, is emitted from the end of the graded-index optical fiber 17, and is reflected from the reflection surface, the optical path thereof is changed by 90 degrees, and the light is irradiated to an organ, thereby forming an image. In addition, the reflection surface is rotated by driving the motor 18 so as to perform OCT scanning such that tomogram of an organ wall is acquired.

As described above, since the flexible substrates 22 and 23 are received along the cutouts 24 and 24, the flexible substrates 22 and 23 are led out to the outside of the motor 18 in the direction, in which the shaft 5 projects, without protruding from the outer diameter of the motor 18. Accordingly, when the motor 18 is mounted in the body of the OCT endoscope probe 15, the flexible substrates 22 and 23 are routed along the longitudinal direction of the OCT endoscope probe 15. Therefore, when the flexible substrates 22 and 23 are routed in the body of the probe 15, the flexible substrates 22 and 23 may not be bent. Accordingly, it is possible to prevent disconnection of the flexible substrates 22 and 23 and to solve generation of R (corner R) of a bent portion generated due to bending. Therefore, it is possible to suppress the increase in diameter of the probe 15 and to shorten an inflexible portion of the front end of the probe 15.

In addition, since the flexible substrates 22 and 23 are received in the cutouts 24 and 24 and are led out to the outside of the motor 18, it is possible to prevent protrusion of the electric power supply wires (flexible substrates 22 and 23) in the diameter direction of the motor 18. Even in this case, it is possible to suppress the increase in diameter of the probe 15.

In addition, since the flexible substrates 22 and 23 are received in the cutouts 24 and 24 and are led out to the outside of the motor 18, it is possible to prevent protrusion of the electric power supply wires in the diameter direction of the motor 18. Therefore, it is possible to suppress the increase in diameter of the probe 15.

Since the flange 21 and the flange 28 function as the shaft bearings, it is possible to reduce the number of parts included in the diameter direction of the motor 18. Therefore, it is possible to further downsize the motor 18 and the probe 15.

In the electric power supply wire, instead of the flexible substrates 22 and 23, for example, a lead wire or a leaf spring type connection terminal may be used. In addition, the connection between the lead wires 43 of the field coil 3 and the electric power supply wires may be performed by a connection terminal, instead of direct fixing using a solder, in the present embodiment. In addition, the probe 15 may be an ultrasonic probe or other probe, instead of the OCT probe.

Figure 21:
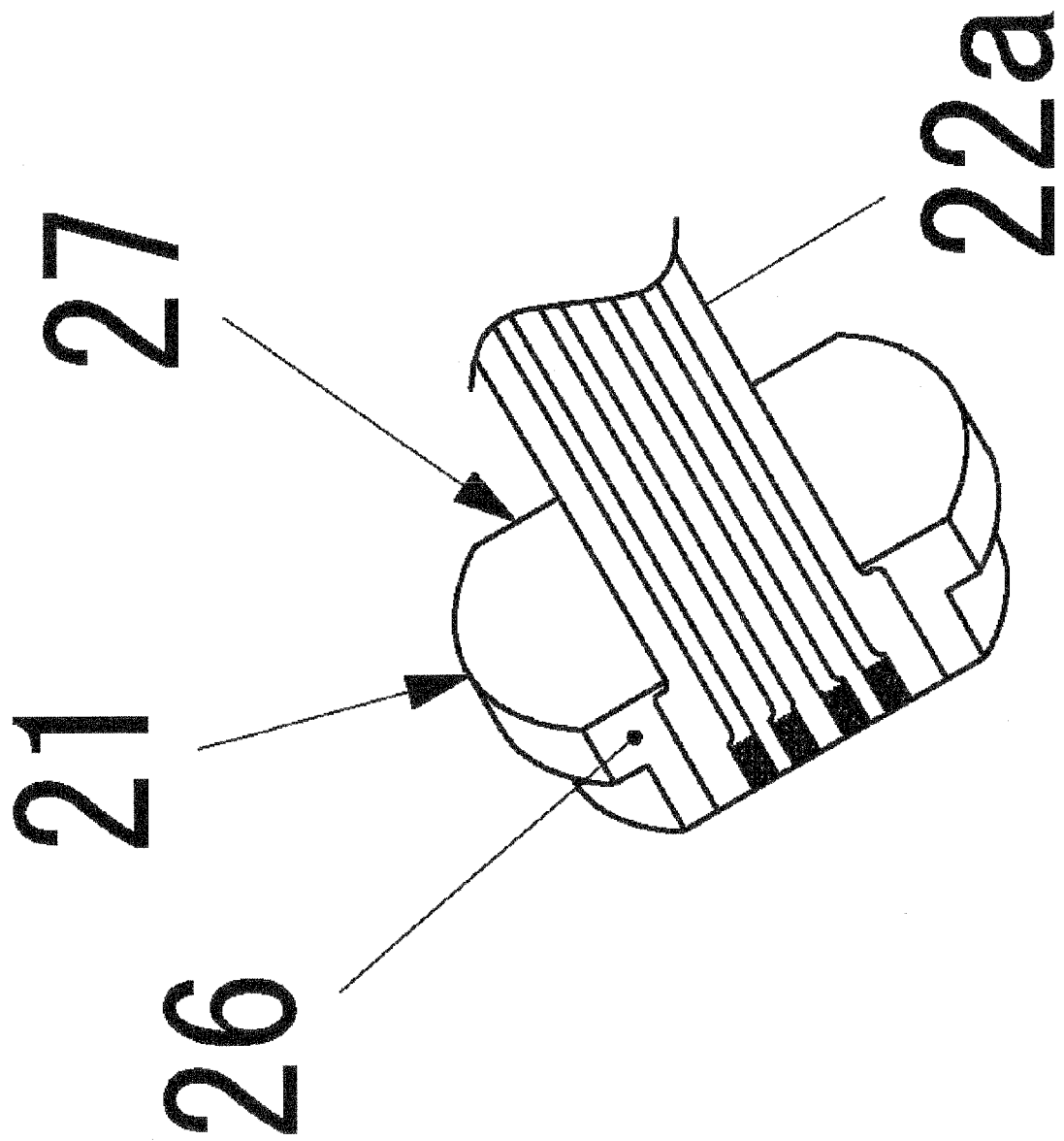
FIG. 21 is a partial enlarged perspective view showing another shape of an electric power supply wire of the motor shown in FIG. 6 or FIG. 9.
Figure 22:
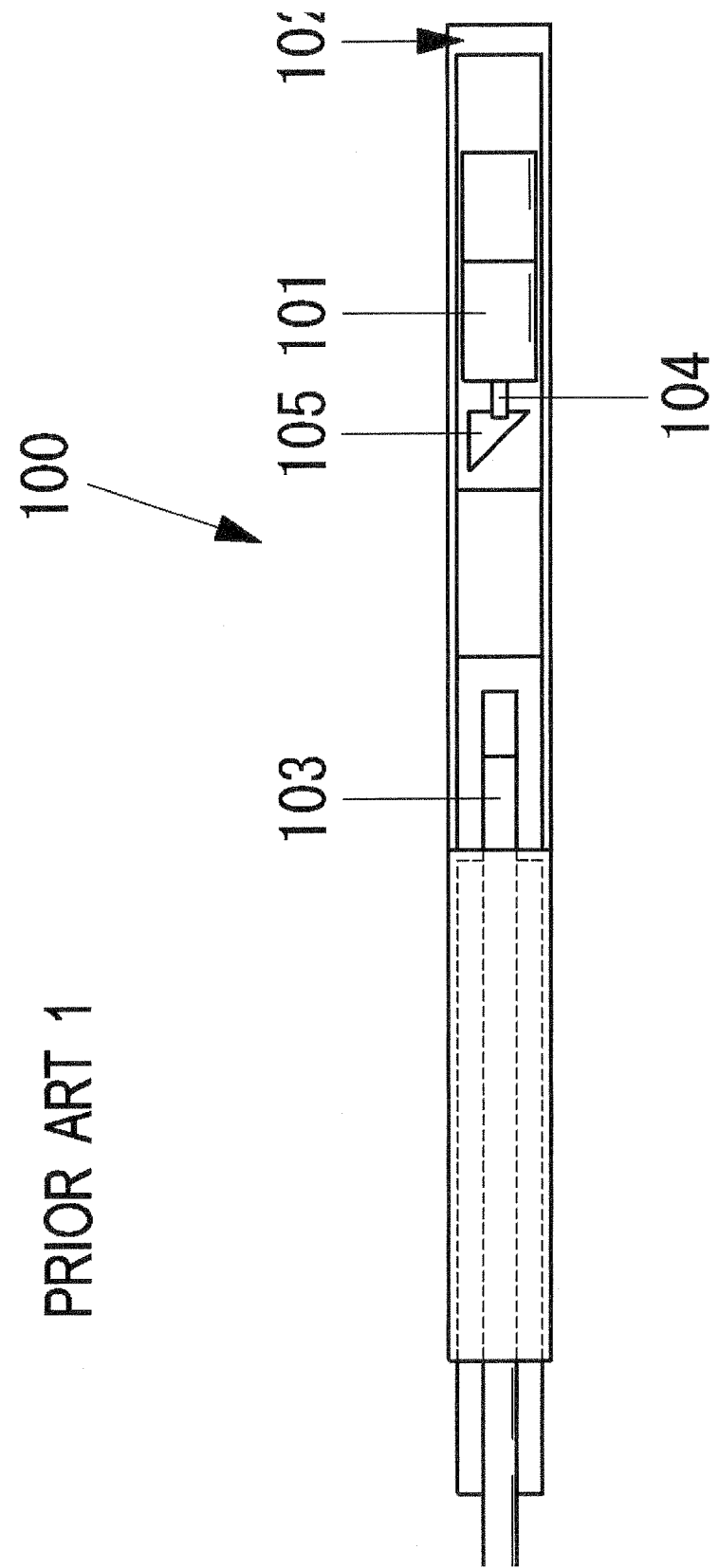
FIG. 22 is a schematic view of the internal structure of a conventional OCT endoscope probe in which a motor is mounted.
Figure 23:
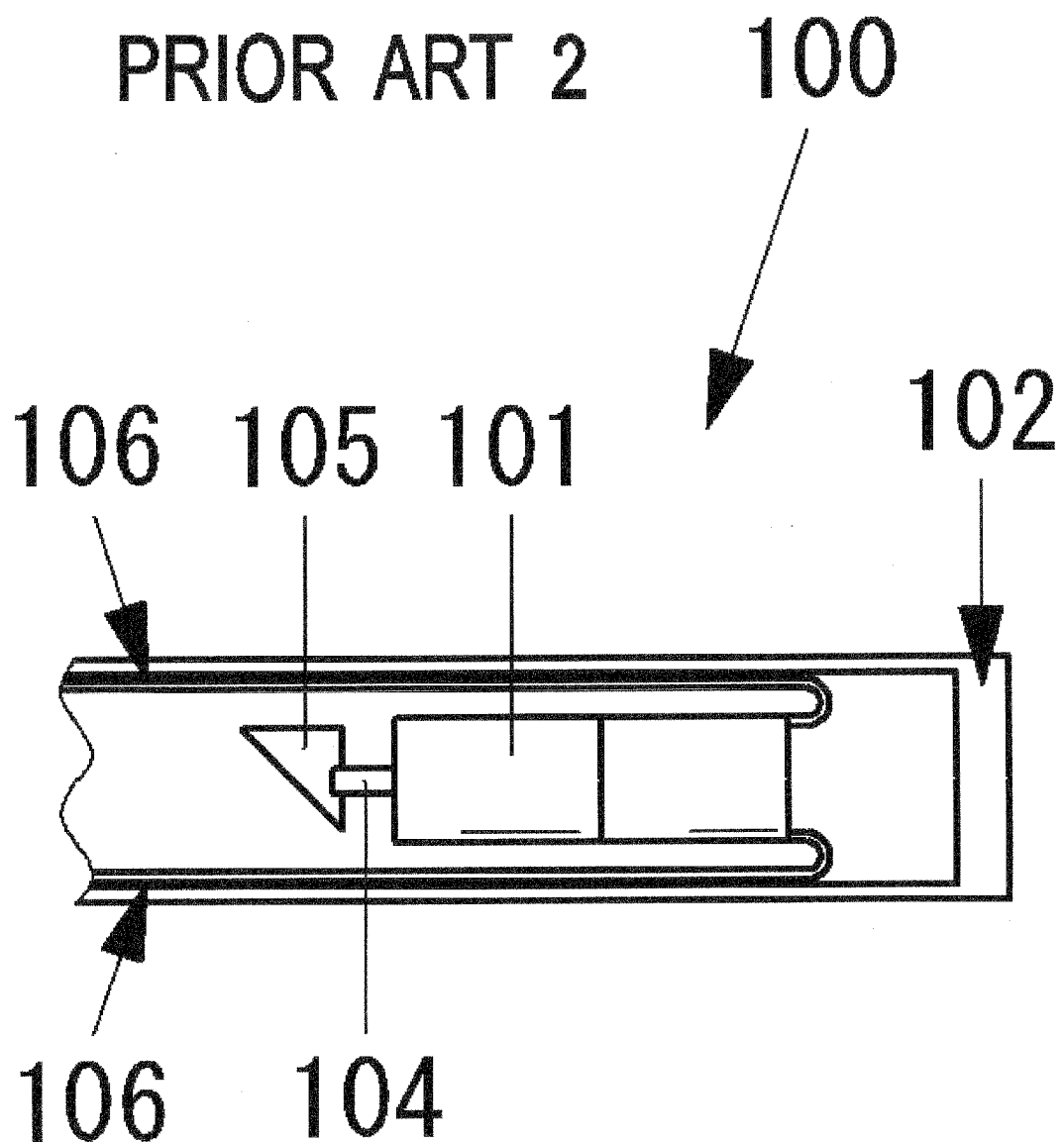
FIG. 23 is a schematic view of the internal structure of a front end of the probe of FIG. 22.

The two flexible substrates 22 and 23 may be changed to be formed of one flexible substrate 22a, as shown in FIG. 21, and the flexible substrate 22a may be led out to the outside of the motor 18. Since the electric power supply wires are led out from only the outer circumference of one side of the motor 18 such that the number of electric power supply wires which become an obstacle at the time of scanning of the probe 15, the rotation angle of the scanning shaft 5 is enlarged. As described above, the flexible substrate 22a may be also replaced with a lead wire or a leaf spring type connection terminal.

As shown in FIGS. 25 and 26, at least a portion or whole of the two flexible substrates 22 and 23 may be changed to be formed of a transparent electrode material 46 which is optically transparent. The portion of the flexible substrates 22 and 23 is the electric power supply wire portion placed on the optical path of the light reflected from the reflection surface of the shaft 5 which is a portion of the motor 18. Accordingly, at the time of scanning of the probe 15, the portion of the transparent electrode material 46 which does not overlap with the flexible substrates 22 and 23 is placed on the optical path of the reflected light. Therefore, it is possible to prevent the electric power supply line from becoming an obstacle at the time of 360-degree scanning of the probe 15. As described above, the flexible substrates 22 and 23 may be replaced with a lead wire or a leaf spring type connection terminal. In addition, the electrical connection between the electric power supply lands 29 and the transparent electrode (ITO- or ZnO-based material) 48 may be performed as shown in FIGS. 28 and 29 or as shown in FIG. 30.

As shown in FIG. 31A or 31B, a high transmissivity material in a wavelength region of the light propagating in the optical fiber 16 may be used as a reinforcing material 51 of the connection portion of the transparent electrode material 46. The fixing of the reinforcing material 51 may be performed by an adhesive, an adhesion tape or the like, which is denoted by a reference numeral 52.

Third Embodiment

Figure 9:
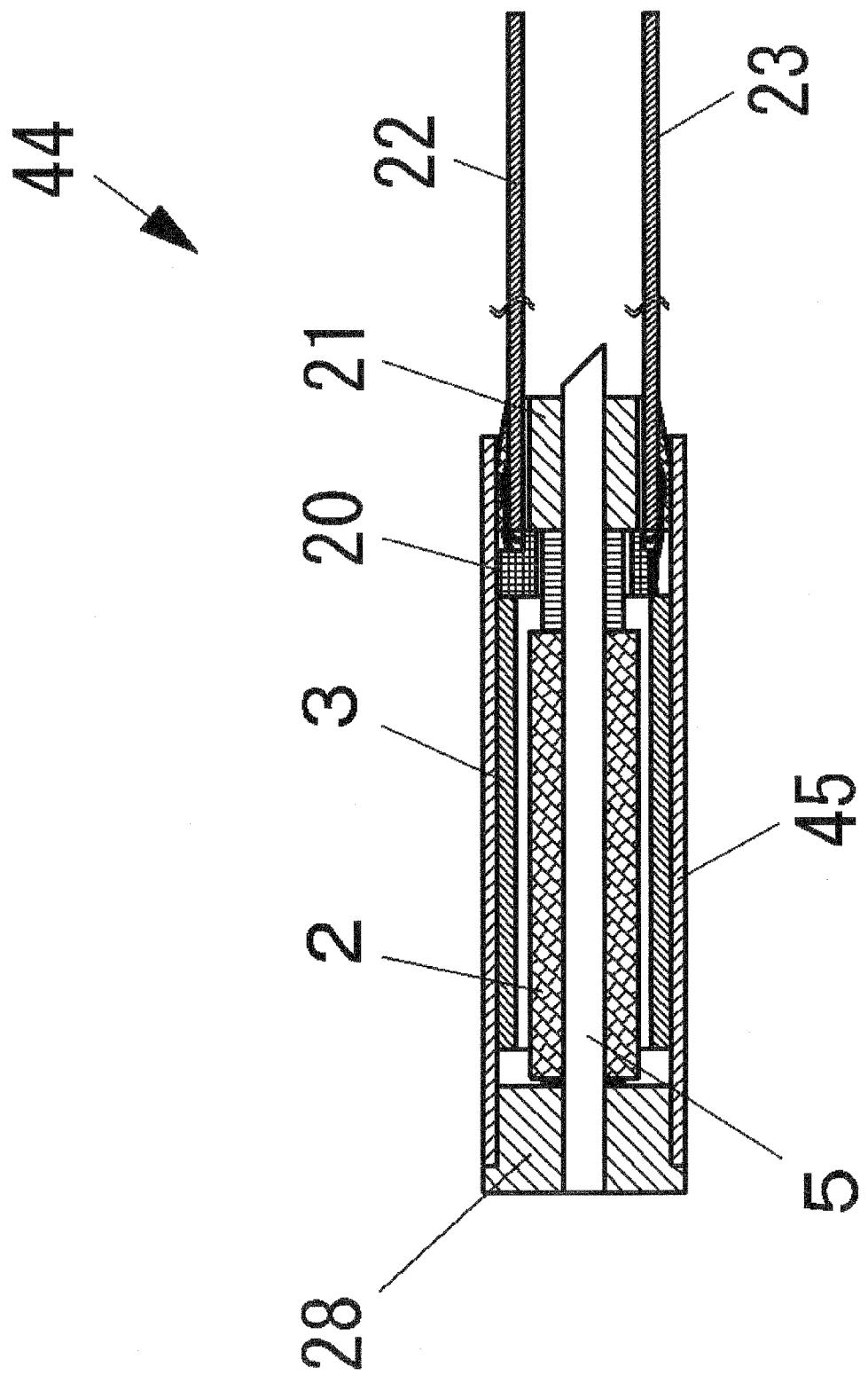
FIG. 9 is a cross-sectional view of a motor according to a third embodiment of the present invention.
Figure 10:
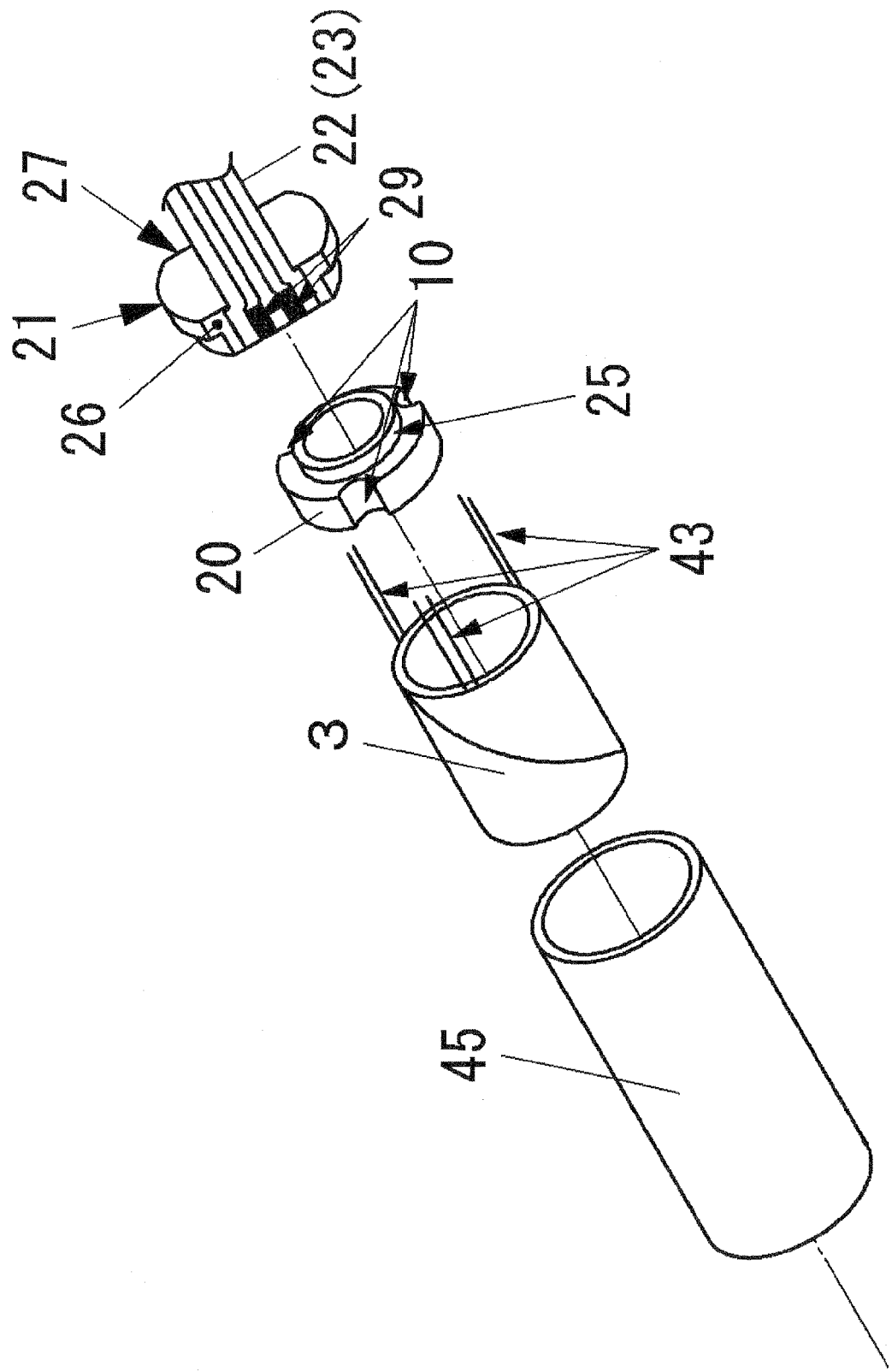
FIG. 10 is an exploded perspective view showing the structure of a stator of the motor of FIG. 9.
Figure 11:
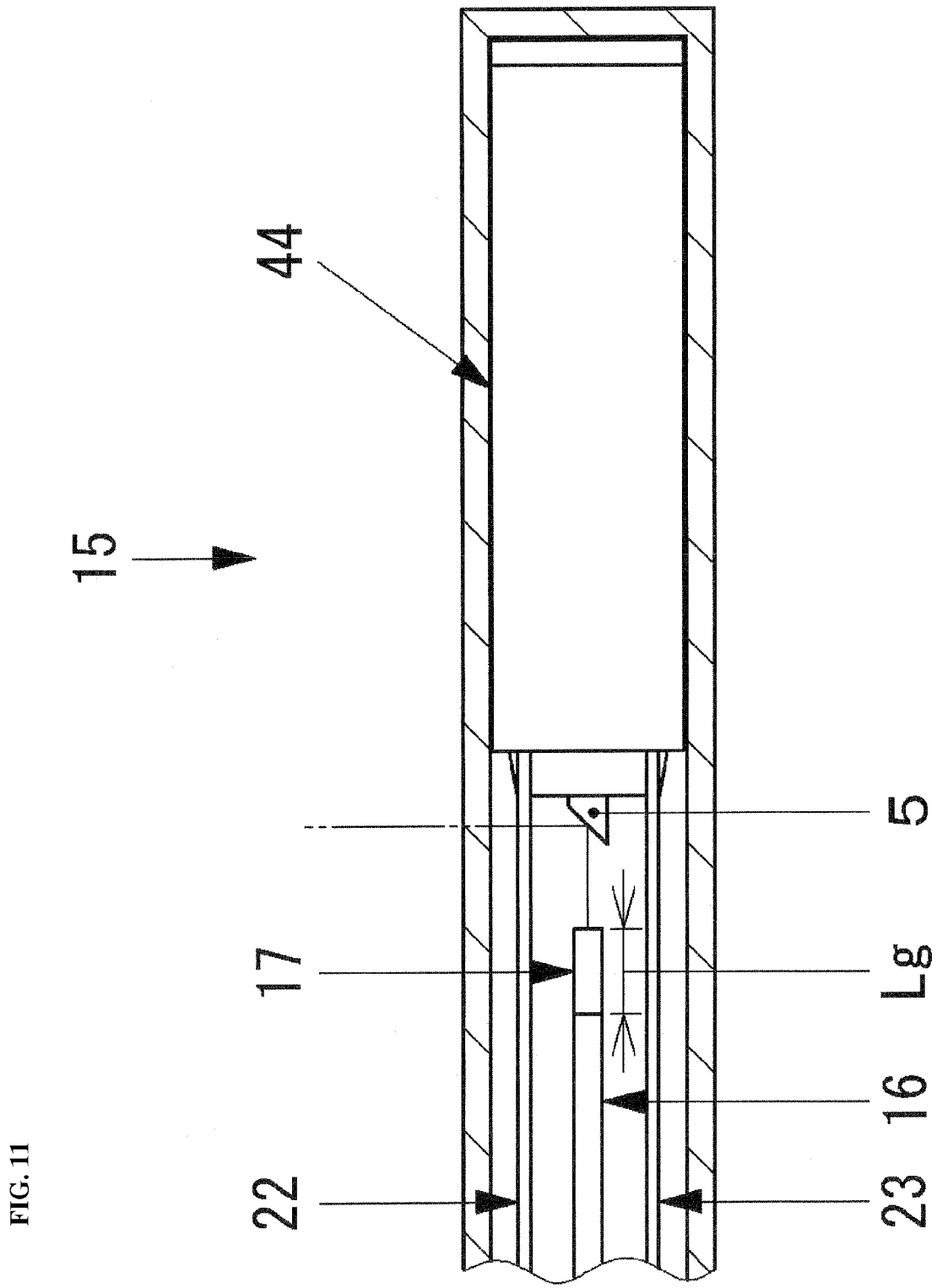
FIG. 11 is a schematic view of the internal structure of an OCT endoscope probe in which the motor of FIG. 9 is mounted.

Hereinafter, a third embodiment of a motor and an OCT endoscope probe according to the present invention will be described in detail with reference to FIGS. 9 to 11. FIG. 9 is a cross-sectional view of the motor according to the third embodiment. FIG. 10 is an exploded perspective view showing the stator structure of the motor in FIG. 9. FIG. 11 is a schematic view of the internal structure of an endoscope probe in which the motor of FIG. 9 is mounted and, more particularly, the OCT endoscope probe. In the description of the motor 44 according to the third embodiment, the portions overlapping with those of the motor 18 of the second embodiment are denoted by the same reference numerals and the description thereof will be omitted or simplified.

The motor 44 of the present embodiment is different from the motor 18 of the second embodiment in that the cutouts 24 and 24 are not formed and thus the appearance of a housing 45 has a substantially cylindrical shape. When the flexible substrates 22 and 23, to which the lead wires (the tap wires and the twisted wires) are connected, are placed on the flat portions 26 and 27 provided on the outer circumferential surface of the flange 21 and the flange 21 is inserted into and fixed to the end of the housing, connection portions between the flexible substrates 22 and 23 and the lead wires are completely received in the housing 45 in the diameter direction of the housing 45. The flexible substrates 22 and 23 are led out to the outside of the motor 44 without extending from the outer diameter of the motor 44 with certainty. The direction in which the flexible substrates 22 and 23 are led out is equal to the direction in which the shaft 5 projects. The motor 44 configured as described above is mounted in the OCT endoscope probe 15 shown in FIG. 11.

As described above, since the flexible substrates 22 and 23 are completely received in the housing 45, the flexible substrates 22 and 23 are led out in the direction, in which the shaft 5 projects to the outside of the motor 44, without protruding from the outer diameter of the motor 44. Accordingly, when the motor 44 is mounted in the body of the OCT endoscope probe 15, the flexible substrates 22 and 23 are routed along the longitudinal direction of the OCT endoscope probe 15. Therefore, when the flexible substrates 22 and 23 are routed in the body of the probe 15, the flexible substrates 22 and 23 may not be bent. Accordingly, it is possible to prevent disconnection of the flexible substrates 22 and 23 and to solve generation of R (corner R) of a bent portion generated due to bending. Therefore, it is possible to suppress the increase in diameter of the probe 15 and to shorten an inflexible portion of the front end of the probe 15.

In the present embodiment, since the flat portions 26 and 27 are formed on the outer circumferential surface of the flange 21, a space is formed between the inner circumferential surface of the housing 45 and the flat portions 26 and 27, and the flexible substrates 22 and 23 which are the electric power supply wires are placed in the space, it is possible to prevent protrusion of the electric power supply wires in the diameter direction of the motor 44. Therefore, it is possible to suppress the increase in diameter of the probe 15.

The two flexible substrates 22 and 23 may be changed to be formed of one flexible substrate 22a, as shown in FIG. 21, and the flexible substrate 22a may be led out to the outside of the motor 44. Since the electric power supply wires are led out from only the circumference of one side of the motor 44 such that the number of electric power supply wires which become an obstacle at the time of scanning of the probe 15 can be reduced, the rotation angle of the scanning shaft 5 is enlarged. As described above, the flexible substrate 22a may be also replaced with a lead wire or a leaf spring type connection terminal.

As shown in FIGS. 25 and 26, at least a portion or whole of the two flexible substrates 22 and 23 may be changed to be formed of a transparent electrode material 46 which is optically transparent. The portion of the flexible substrates 22 and 23 is the electric power supply wire portion placed on the optical path of the light reflected from the reflection surface of the shaft 5 which is a portion of the motor 18. Accordingly, at the time of scanning of the probe 15, the portion of the transparent electrode material 46 which does not overlap with the flexible substrates 22 and 23 is placed on the optical path of the reflected light. Therefore, it is possible to prevent the electric power supply line from becoming an obstacle at the time of 360-degree scanning of the probe 15. As described above, the flexible substrates 22 and 23 may be replaced with a lead wire or a leaf spring type connection terminal. In addition, the electrical connection between the electric power supply lands 29 and the transparent electrode (ITO- or ZnO-based material) 48 may be performed as shown in FIGS. 28 and 29 or as shown in FIG. 30.

As shown in FIG. 31A or 31B, a high transmissivity material in a wavelength region of the light propagating in the optical fiber 16 may be used as a reinforcing material 51 of the connection portion of the transparent electrode material 46. The fixing of the reinforcing material 51 may be performed by an adhesive, an adhesion tape or the like, which is denoted by a reference numeral 52.

Fourth Embodiment

Figure 12:
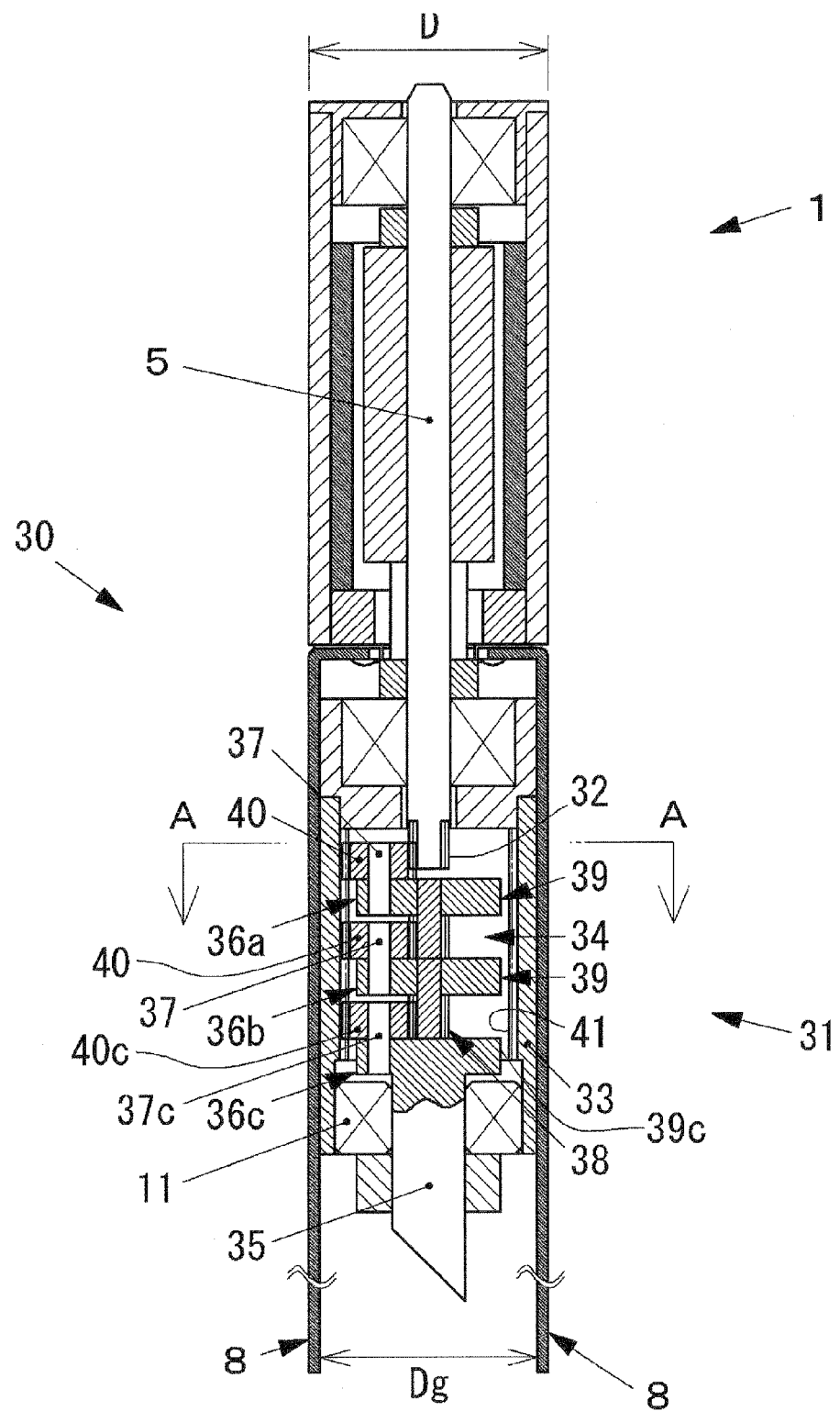
FIG. 12 is a cross-sectional view of a geared motor according to a fourth embodiment.
Figure 13:
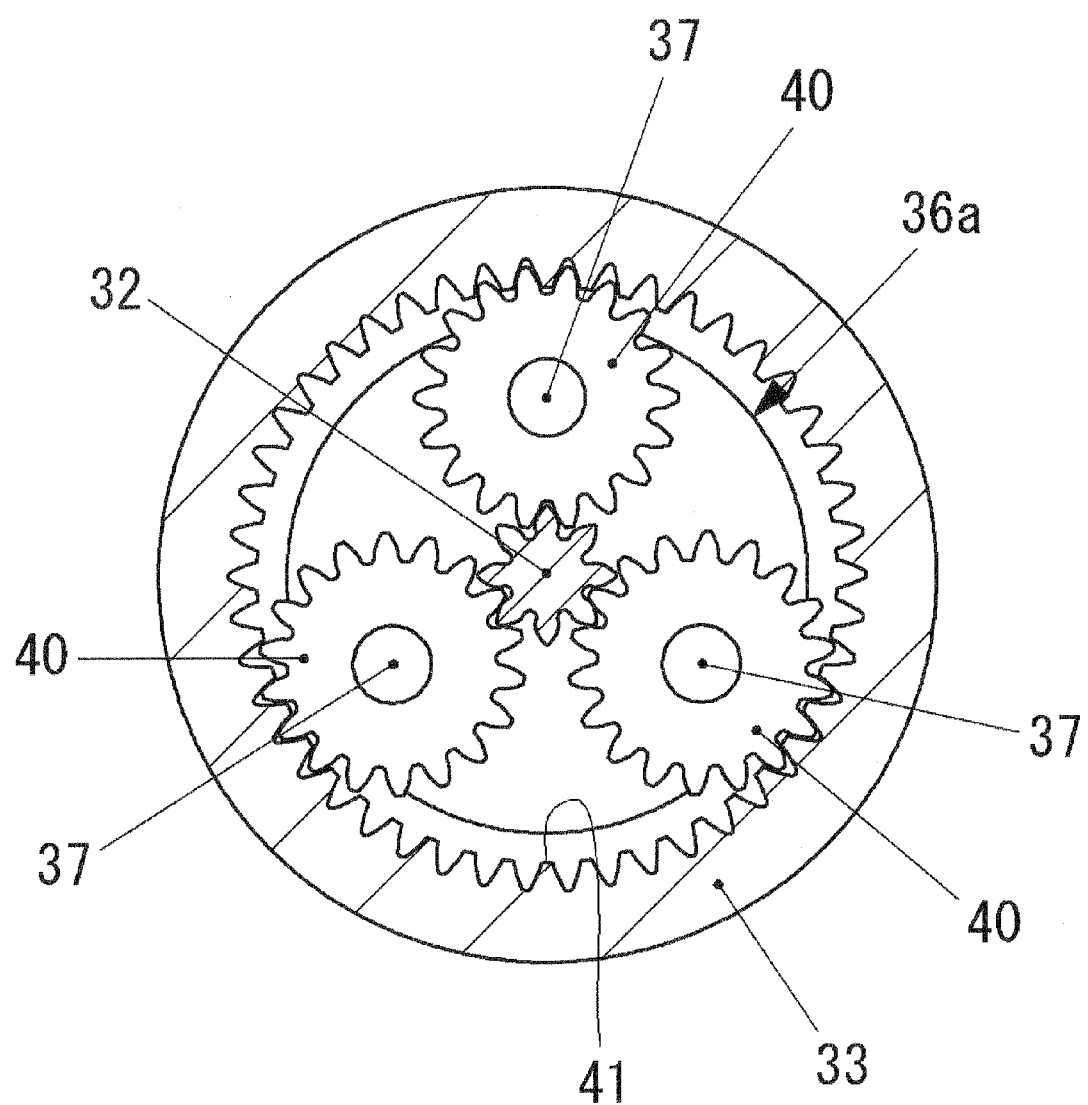
FIG. 13 is a cross-sectional view taken along line A-A of FIG. 12.
Figure 14:
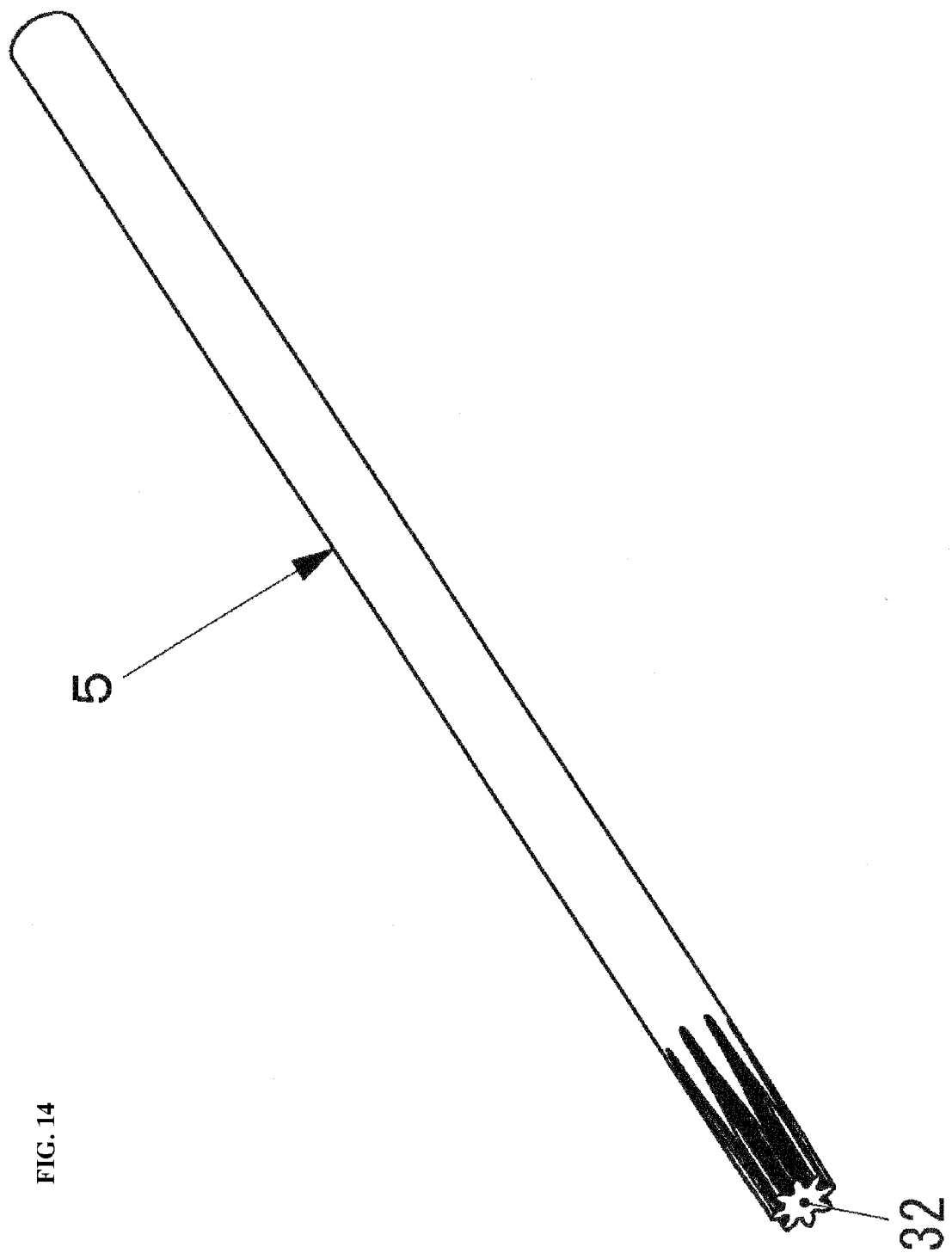
FIG. 14 is a shaft perspective view showing a pinion formed on an end of a shaft of the motor of FIG. 12.
Figure 15:
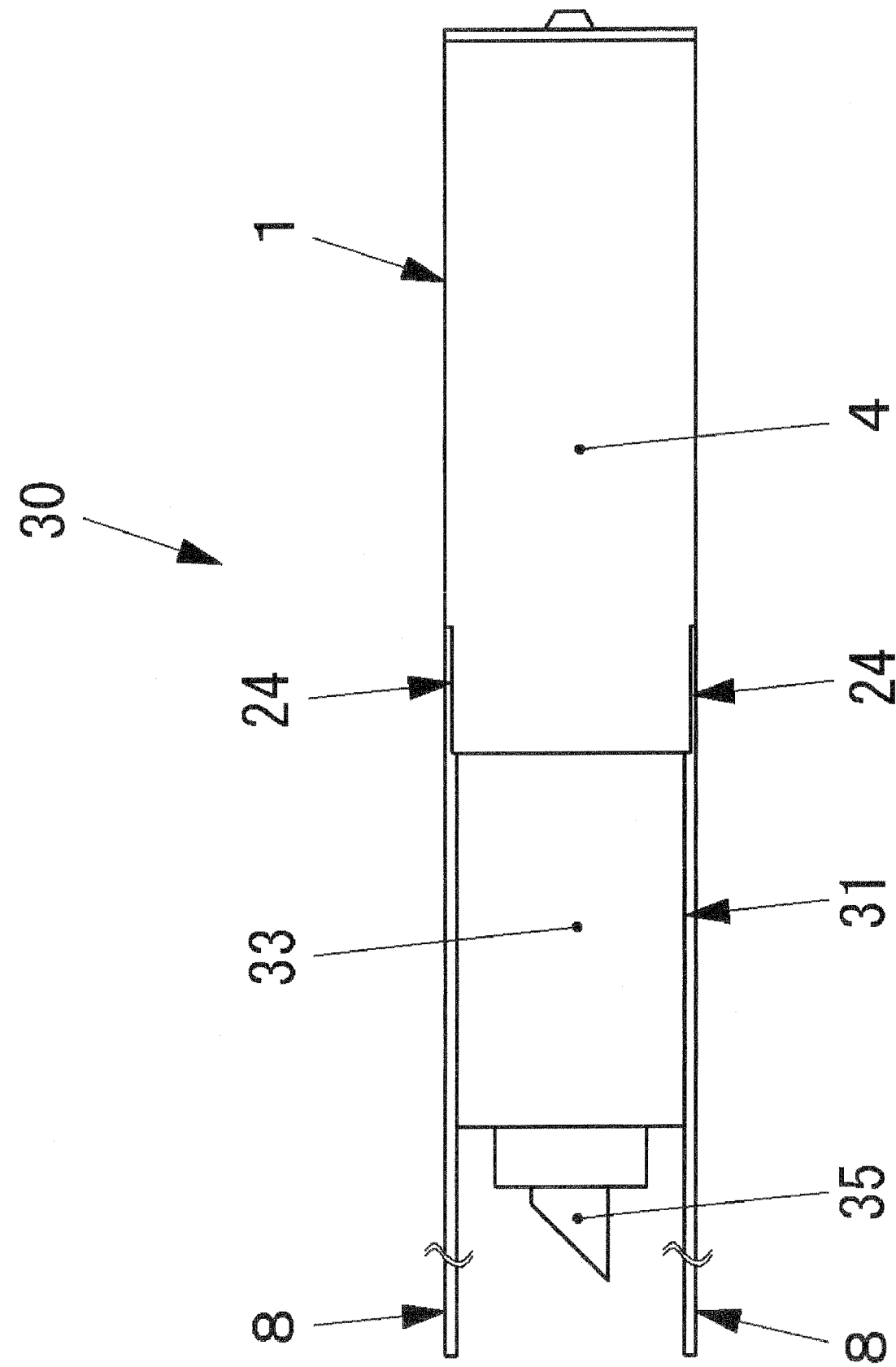
FIG. 15 is a side view of the geared motor of FIG. 12.
Figure 16:
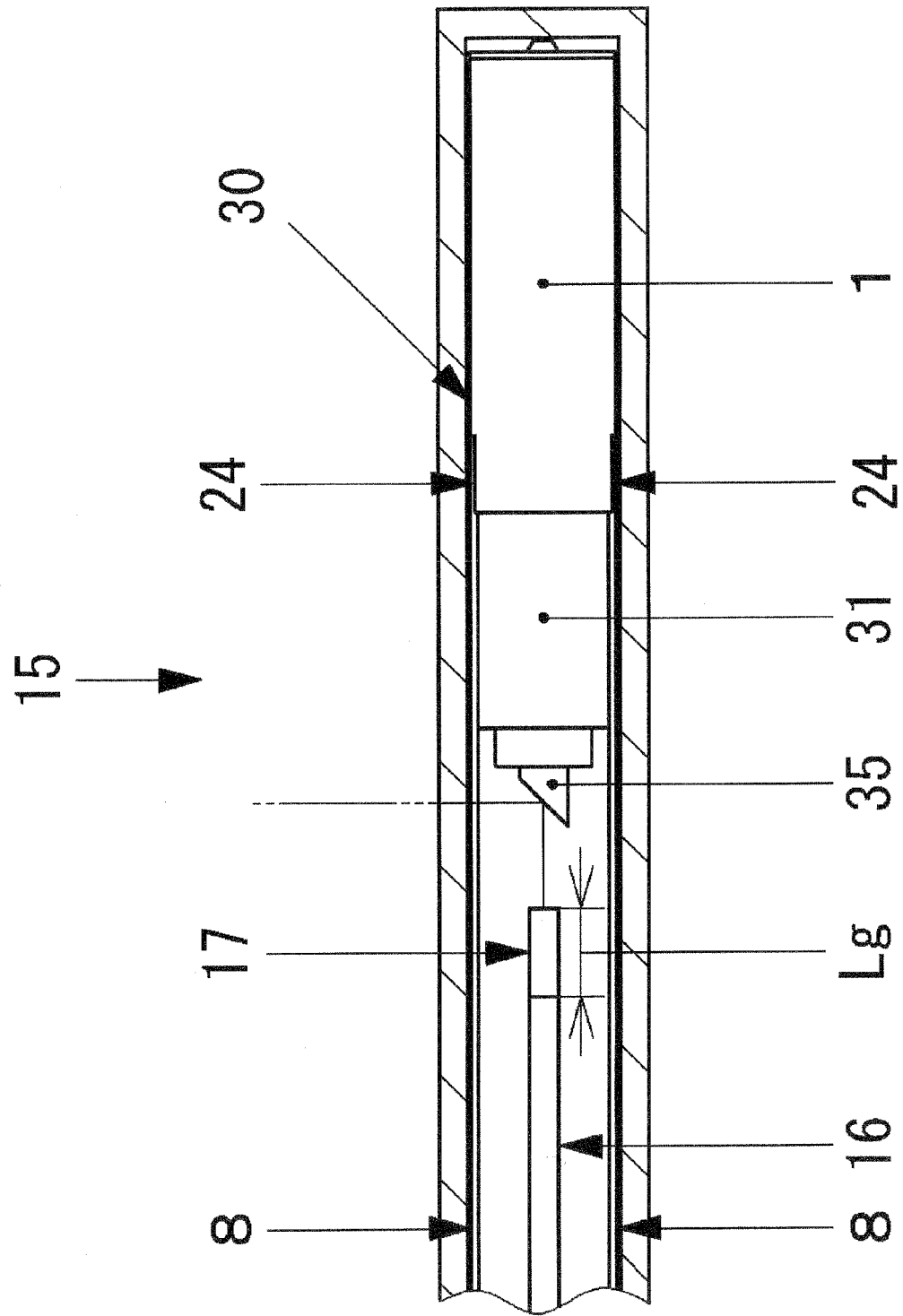
FIG. 16 is a schematic view of the internal structure of an OCT endoscope probe in which the geared motor of FIG. 12 is mounted.
Figure 20:
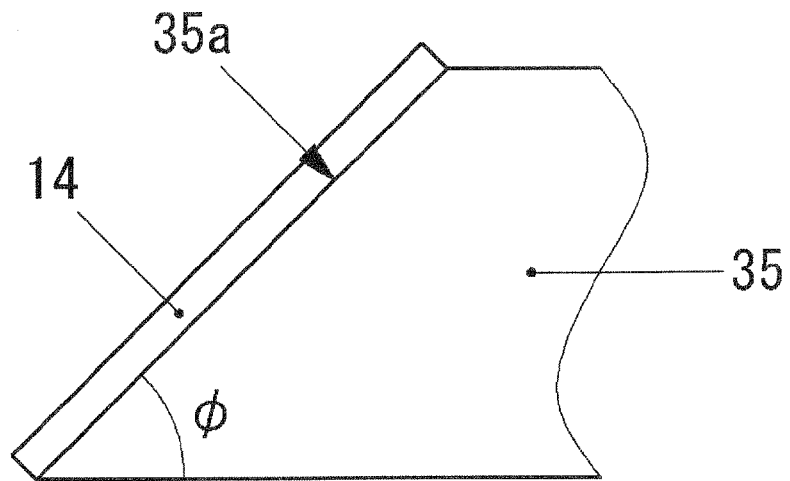
FIG. 20A is a partial enlarged view of an end of an output shaft of the geared motor of FIG. 12 and is a partial enlarged view showing the end of the output shaft in which a reflective film is formed on an obliquely formed surface.
FIG. 20B is a partial enlarged view of the end of the output shaft of the geared motor of FIG. 12 and is a partial enlarged view showing the end of the output shaft in which the obliquely formed surface is subjected to mirror polishing.
Figure 20:
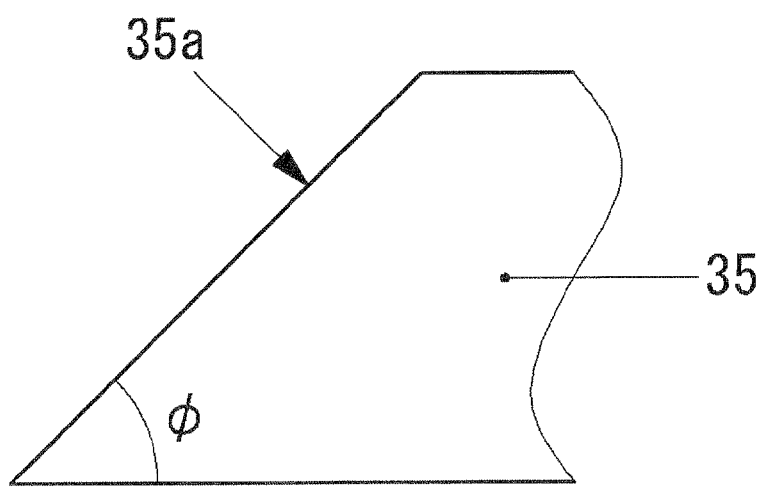

Hereinafter, a fourth embodiment of a motor and, more particularly, a geared motor in which a gear head is mounted, and an OCT endoscope probe according to the present invention will be described in detail with reference to FIGS. 12 to 16 and 20. FIG. 12 is a cross-sectional view of the geared motor according to the fourth embodiment. FIG. 13 is a cross-sectional view taken along line A-A of FIG. 12. FIG. 14 is a shaft perspective view showing a pinion formed on an end of a shaft of the motor. FIG. 16 is a schematic view of the internal structure of an endoscope probe in which the geared motor of FIG. 12 is mounted and, more particularly, an OCT endoscope probe. FIGS. 20A and 20B are partial enlarged views of an end of an output shaft of the geared motor of FIG. 12. The same portions as the first embodiment are denoted by the same reference numerals and the description thereof will be omitted or simplified.

In FIG. 12, the geared motor 30 includes a motor 1 and a gear head 31. In the drawings, a reference numeral 1 denotes the motor and a reference numeral 31 denotes the reduction gear head driven by and connected to the motor 1 via a pinion 32 formed on the shaft 5. In the present embodiment, the structure of the motor 1 is any one of the structures of FIGS. 1, 6 and 9 (in FIG. 12, for example, the motor 1 of FIG. 1 is shown).

In FIGS. 12 and 14, the pinion 32 having an outer diameter equal to or less than that of the shaft 5 is integrally formed on an end of the shaft 5. Generally, the pinion 32 is formed by performing cutting such as hobbing, rolling, or the like to the shaft 5, but the pinion 32 can be formed by the other suitable method, for example, a method of adhering a member, in which the pinion is formed, to the front end of the motor shaft.

If the shaft 5 is subjected to the cutting or the rolling so as to form the pinion 32, a member for the shaft 5 formed of a round bar such as stainless steel is subjected to centerless machining so as to adjust outer diameter precision and surface roughness, the pinion 32 is formed on the end thereof by the cutting, the rolling or the like, and the shaft 5 including the pinion 32 is finished by heating treatment, barrel polishing treatment or the like. In addition, a position where the pinion 32 is formed may not be necessarily the extremity of the shaft 5.

In the present embodiment, the outer diameter of the pinion 32 is equal to or less than that of the shaft 5 in order to decrease the diameter of the pinion so as to obtain a large reduction ratio. The lower limit of the outer diameter of the pinion 32 is not specially limited, but is preferably at least 80% of the outer diameter of the shaft 5 in view of strength.

The reduction gear head 31 includes a housing 33, a reduction gear mechanism 34 driven by and connected to the pinion 32, and an output shaft 35 placed on the output side (front end side) such that the rotation thereof is freely supported on a shaft bearing 11. The pinion 32 is engaged with an initial stage gear of the reduction gear mechanism 34. The structure of the reduction gear mechanism 34 included in the reduction gear head 31 is arbitrarily set and various mechanisms may be applied. However, in the present embodiment, a planetary gear reduction mechanism is used. The basic structure of the planetary gear reduction mechanism includes two sets of independent carrier units 36a and 36b sequentially placed from the side of the motor 1 to the side of the output shaft 35 and a set of carrier units 36c formed on the base end of the output shaft 35.

Each of the carrier units 36a and 36b includes a plate-shape carrier 39, in which three shaft portions 37 for supporting the planetary gear protrude on the surface of the side of the motor 1 in a circumferential direction at an interval of 120° and a sun gear 38 protrudes on a central portion of the surface of the side opposite to the motor 1, and planetary gears 40 of which the rotation is freely supported on the shaft portions 37 (planetary gears 40 placed in the circumferential direction at an interval of 120°). The carrier unit 36c includes a plate-shape carrier 39c, in which three shaft portions 37c for supporting the planetary gear protrude on the surface of the side of the motor 1 in the circumferential direction at an interval of 120° and the output shaft 35 is fixed to the base end (or integrally formed with the base end) on the central portion of the surface of the side opposite to the motor 1, and a planetary gear 40c of which the rotation is freely supported on the shaft portions 37c. An internal gear 41 is formed on the inner surface of the housing 33 in which the reduction gear mechanism 34 is placed.

As described above, the planetary gears 40 and 40c of the carrier units 36a to 36c are engaged with the internal gear 41, the sun gear 38 of the carrier unit of the side of the motor 1 is engaged with the three planetary gears 40 and 40c of the carrier unit of the side opposite to the motor 1 in the adjacent carrier units, and the pinion 32 formed on the shaft 5 of the motor is engaged with the three planetary gears 40 of the first stage carrier unit 36a. Accordingly, the rotation of the pinion 32 is sent to the output shaft 35 via the three carrier units 36a to 36c.

In the geared motor 30, as shown in FIGS. 12 and 20, the end of the output shaft 35 is obliquely cut to the axial direction of the output shaft 35 such that the end of the output shaft 35 is obliquely formed to the axial direction of the output shaft 35. The cutting angle Φ may be set to a desired angle by the requirement characteristics of the OCT endoscope probe in which the geared motor 30 is mounted. In the present embodiment, the cutting angle is, for example, 45 degrees.

In an obliquely formed surface 35a of the output shaft 35, a reflective film 14 is formed (see FIG. 20A) or mirror polishing is performed (see FIG. 20B) such that a light reflection surface is formed. If the mirror polishing is performed, the obliquely formed surface 35a is mechanically polished so as to perform mirror finishing. In addition, if the reflective film 14 is formed, a metal film or a dielectric multi-layer film with high reflectivity, such as aluminum, nickel, gold or silver, is formed on the obliquely formed surface 35a. As the film forming method, deposition, sputtering, CVD, plating, coating or the like may be used.

Alternatively, the overall output shaft 35 may be formed of amorphous metal alloy. By such a configuration, the reflection surface is formed of the amorphous metal alloy, but the surface roughness Ry of the reflection surface is set to 0.4 μm or less and more preferably 0.1 μm or less. By setting the surface roughness Ry to the above range, it is possible to prevent light reflection efficiency of the reflection surface from deteriorating.

As the amorphous metal alloy, amorphous metal alloy having at least one of elements such as Fe, Ni, Cu, Ti and Zr as main components is preferably used.

If the overall output shaft 35 is formed of amorphous metal alloy, the overall output shaft 35 is manufactured by injection molding. In particular, it is preferable that polishing is performed to a mold for molding the reflection surface and the mold surface roughness Ry is set to 0.4 μm or less and, more particularly, 0.1 μm or less, because the light reflection efficiency of the reflection surface after transferring is prevented from deteriorating as described above.

Alternatively, the light reflection surface may be formed in the obliquely formed surface 35a by combining the technical elements, for example, mirror-polishing the obliquely formed surface 35a of the output shaft 35 and forming the reflective film 14 on the obliquely formed surface 35a. In addition, the light reflection surface may be formed in the obliquely formed surface 35a by forming the overall output shaft 35 using amorphous metal alloy, setting the surface roughness Ry of the obliquely formed surface 35a of the output shaft 35 to 0.4 μm or less and forming the reflective film 14 on the obliquely formed surface 35a.

The outer diameter D of the motor 1 is set to about 2 mm as described above, but the outer diameter Dg of the gear head 31 is preferably set to be less than the outer diameter D of the motor 1. This is because the electric power supply wires (flexible substrates 8 and 8) led out from the motor 1 can be led to the outside of the motor 1 in the direction in which the output shaft 35 of the gear head 31 projects, without protruding in the outer diameter direction in the outer circumferential portion of the housing 33 of the gear head 31 and thus the increase in diameter of the probe 15 can be suppressed.

Figure 17:
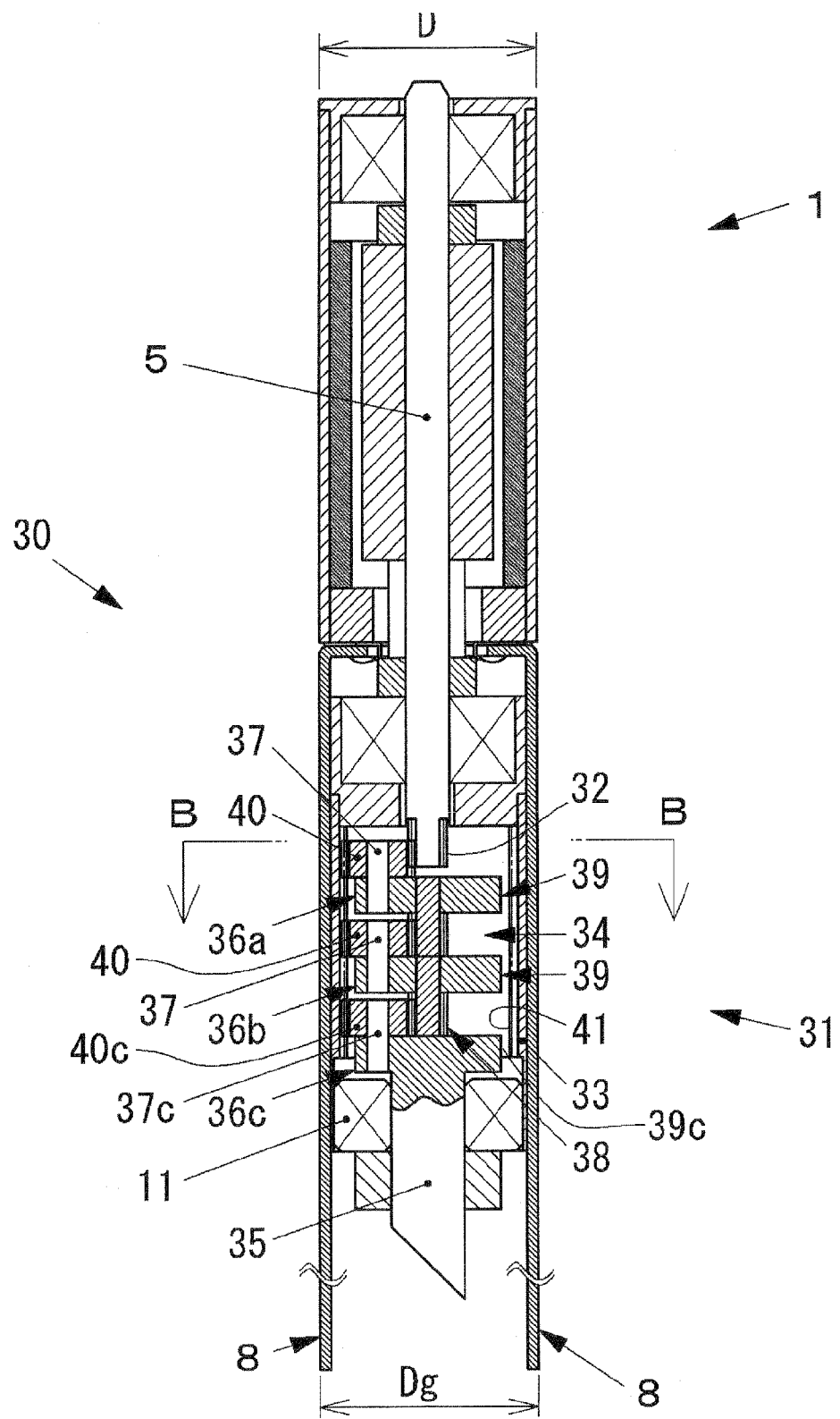
FIG. 17 is a cross-sectional view of a geared motor according to another example of the fourth embodiment.
Figure 18:
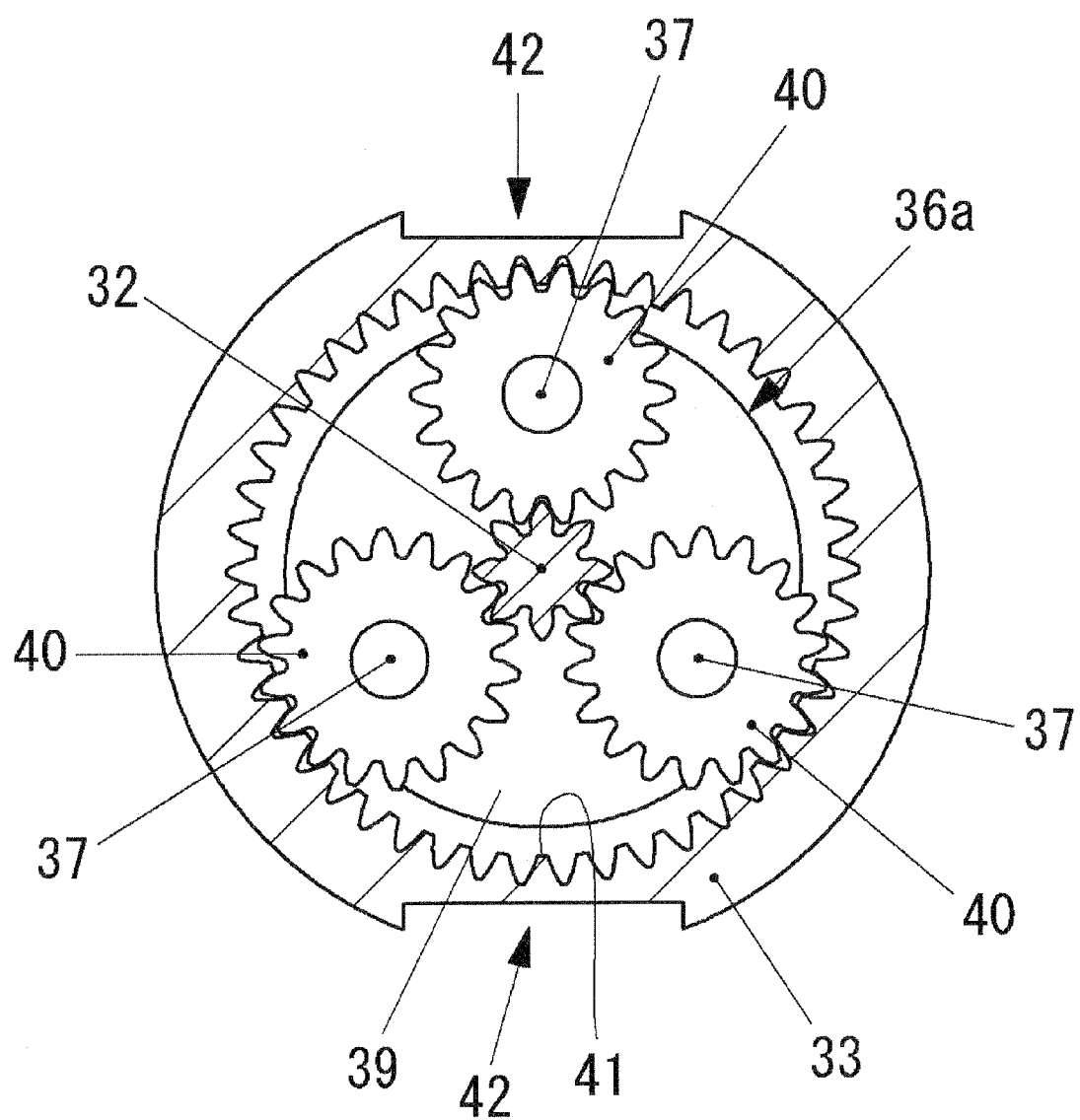
FIG. 18 is a cross-sectional view taken along line B-B of FIG. 17.
Figure 19:
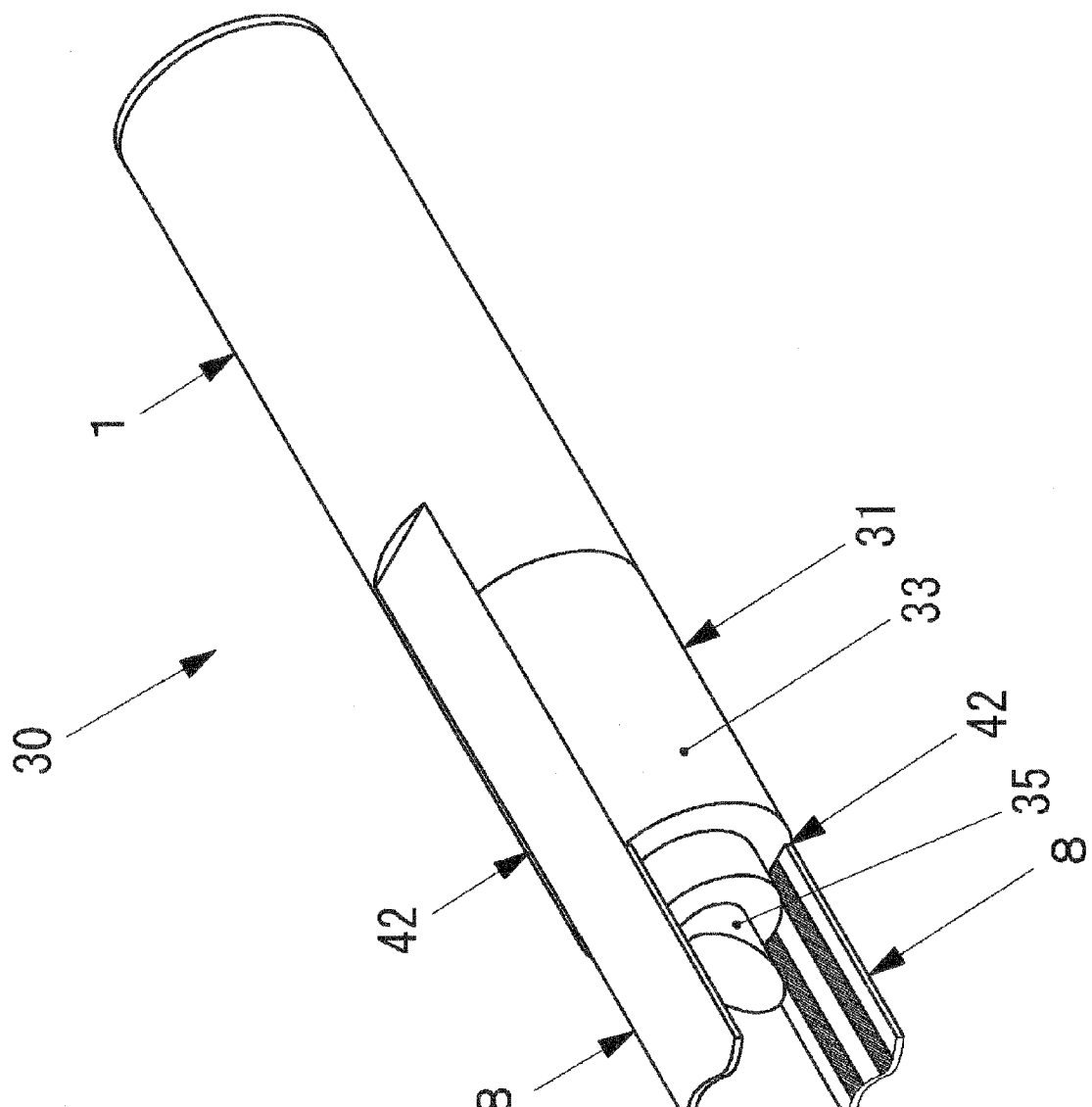
FIG. 19 is a perspective view showing the geared motor of FIG. 17.

If the outer diameter Dg of the gear head 31 is set to be equal to the outer diameter D of the motor 1 or is set to be equal to or more than the outer diameter D of the motor, as shown in FIGS. 17 to 19, electric power supply wire receiving grooves 42 and 42 may be formed in the housing 33 of the gear head 31, the flexible substrates 8 and 8 may be received in the electric power supply receiving grooves 42 and 42, and the flexible substrates 8 and 8 may be led out to the outside of the motor 1 in the direction in which the output shaft 35 of the gear head 31 projects. By such a configuration, even when the outer diameter Dg of the gear head 31 is set to be equal to or more than the outer diameter D of the motor 1, it is possible to prevent protrusion of the electric power supply wires to the outer circumference of the gear head 31. Therefore, it is possible to suppress the increase in diameter of the probe 15.

The geared motor 30 configured as described above is mounted in the OCT endoscope probe 15 shown in FIG. 16. The geared motor 30 is placed on the distal portion in the body of the OCT endoscope probe 15.

When the geared motor 30 is placed in the body of the OCT endoscope probe 15, the direction in which the output shaft 35 projects to the outside of the geared motor 30 is opposite to the direction of the front end of the OCT endoscope probe 15. By placing the geared motor 30 as described above, the reflection surface of the end of the output shaft 35 faces the end of the optical fiber 16. When the geared motor 30 is mounted in the body of the OCT endoscope probe 15, the flexible substrates 8 and 8 are routed along the longitudinal direction of the OCT endoscope probe 15.

Accordingly, when the electric power supply wires (the flexible substrates 8 and 8) are routed in the body of the probe 15, the electric power supply wires may not be bent. Accordingly, it is possible to prevent disconnection of the electric power supply wires and to solve generation of R (corner R) of a bent portion generated due to bending. Therefore, it is possible to suppress the increase in diameter of the probe 15 and to shorten an inflexible portion of the front end of the probe 15.

If the motor 1 of the geared motor 30 is replaced with the motor 18 or the motor 44, the two flexible substrates 22 and 23 may be changed to be formed of one flexible substrate 22a, as shown in FIG. 21, and the flexible substrate 22a may be led out to the outside of the motor 18 or 44. Since the electric power supply wires are led out from only the outer circumference of one side of the motor 18 or 44 such that the number of electric power supply wires which become an obstacle at the time of scanning of the probe 15 can be reduced, the rotation angle of the scanning output shaft 35 is enlarged.

In addition, the electric power supply wires, instead of the flexible substrates 8 and 8, for example, a lead wire or a leaf spring type connection terminal may be used. Accordingly, the flexible substrate 22a may be also replaced with the lead wire or the leaf spring type connection terminal.

As shown in FIGS. 25 and 26, at least a portion or whole of the two flexible substrates 8 and 8 may be changed to be formed of a transparent electrode material 46 which is optically transparent. The portion of the flexible substrates 8 and 8 is the electric power supply wire portion placed on the optical path of the light reflected from the reflection surface of the output shaft 35 which is a portion of the geared motor 30. Accordingly, at the time of scanning of the probe 15, the portion of the transparent electrode material 46 which does not overlap with the flexible substrates 8 and 8 is placed on the optical path of the reflected light. Therefore, it is possible to prevent the electric power supply line from becoming an obstacle at the time of 360-degree scanning of the probe 15. As described above, the flexible substrates 8 and 8 may be replaced with a lead wire or a leaf spring type connection terminal. In addition, the electrical connection between the electric power supply lands 13 of the flexible substrates 8 and the transparent electrode (ITO- or ZnO-based material) 48 may be performed as shown in FIGS. 28 and 29 or as shown in FIG. 30.

As shown in FIG. 31A or 31B, a high transmissivity material in a wavelength region of the light propagating in the optical fiber 16 may be used as a reinforcing material 51 of the connection portion of the transparent electrode material 46. The fixing of the reinforcing material 51 may be performed by an adhesive, an adhesion tape or the like, which is denoted by a reference numeral 52.

As described above, according to the present embodiment, since the end of the output shaft 35 of the geared motor 30 is formed by the light reflection surface, an optical part for a scanner, such as a mirror or a prism, is unnecessary in the end of the output shaft 35. Accordingly, a space occupied by the scanner in the internal space of the front end of the probe can be eliminated and the inflexible portion of the front end of the OCT endoscope probe 15 can be shortened. In addition, the number of parts can be reduced.

Since the light reflection surface is directly formed in the end of the output shaft 35, the optical path of the light after being reflected from the reflection surface can be set by desire and efficient light transmission to the subject can be achieved.

In addition, since a separate part such as the optical part for the scanner is not attached to the output shaft 35 of the geared motor 30, it is possible to rotate the output shaft 35 with low torque and suppress the increase in size of the geared motor 30. Accordingly, it is possible to suppress the increase in diameter of the overall OCT endoscope probe 15.

By removing the optical part for the scanner, it is possible to reduce one axial shift element between the core axis of the optical fiber 16 and axis of the geared motor 30.

By forming the reflective film 14 in the end of the output shaft 35 or performing mirror polishing, the light reflection efficiency of the end of the output shaft 35 is improved and thus light propagation efficiency is also improved.

Since the amorphous metal alloy does not have a crystal grain boundary, it is possible to improve surface smoothness of the reflection surface by forming the overall output shaft 35 using the amorphous metal alloy. Accordingly, since the amorphous metal alloy has a good mold transfer property in the injection molding process or a good polishing property in the polishing process, surface smoothness is excellent. As a result, the reflection efficiency of the manufactured reflection surface is also improved and the light propagation efficiency is also improved.

In addition, by mirror-polishing the obliquely formed surface 35a of the output shaft 35 and forming the reflective film 14 on the obliquely formed surface 35a so as to form the light reflection surface on the obliquely formed surface 35a or forming the overall output shaft 35 using the amorphous metal alloy, setting the surface roughness Ry of the obliquely formed surface 35a of the output shaft 35 to 0.4 μm or less and forming the reflective film 14 on the obliquely formed surface 35a so as to form the light reflection surface on the obliquely formed surface 35a, the obliquely formed surface 35a on which the reflective film 14 is formed is mirror-formed and the reflective film 14 is then formed. Accordingly, it is possible to further improve the reflection efficiency of the reflection surface.

The probe 15 may be an ultrasonic probe or other probe, instead of the OCT probe. When the geared motor 30 is placed in the ultrasonic endoscope probe body, the direction in which the output shaft 35 projects to the outside of the geared motor 30 is opposite to the direction of the front end of the ultrasonic endoscope probe, such that the reflection surface of the end of the output shaft 35 faces an ultrasonic vibrator.

Instead of that the reflection surface is not formed on the end of the output shaft 35, a geared motor in which the ultrasonic vibrator is fixed may be changed to be placed in the ultrasonic endoscope probe body. Even when such a geared motor is placed, the direction in which the output shaft projects to the outside of the geared motor is opposite to the direction of the front end of the ultrasonic endoscope probe.

As described above, when the electric power supply wires are routed in the ultrasonic endoscope probe body, the electric power supply wires may not be bent. Accordingly, it is possible to prevent disconnection of the electric power supply wires and to solve generation of R (corner R) of a bent portion generated due to bending. Therefore, it is possible to suppress the increase in diameter of the ultrasonic endoscope probe and to shorten an inflexible portion of the front end of the ultrasonic endoscope probe.

Industrial Availability

The motor and the geared motor of the present invention are applicable to the endoscope probe in a medical field.

What is claimed is:

1. A motor, comprising:
   a magnet, a field coil, a housing having a first distal end and a second distal end, an electric power supply wire, a shaft having a first end is disposed in a longitudinal direction as the housing and projected from the first distal end of the housing,
   a lead wire led out from the field coil and connected to the electric power supply wire, and
   a cutout formed in the first distal end of the housing,
   wherein the electric power supply wire connected with the lead wire is received along the cutout and led out to outside of the motor in the longitudinal direction in which the shaft projects, which is toward the first distal end of the housing where the cutout is formed, and
   the first end of the shaft, which projects from the first distal end of the housing, is obliquely formed in an axial direction of the shaft.

2. The motor according to claim 1, further comprising a first flange and a second flange, each respectively fixed to each distal end of the housing, and one or both of the flanges functions as a shaft bearing.

3. The motor according to claim 1, wherein at least a portion of the electric power supply wire is formed of a transparent electrode material.

4. The motor according to claim 1, wherein
   a reflective film is formed on an obliquely formed surface of the first end of the shaft such that a light reflection surface is formed in the obliquely formed surface.

5. The motor according to claim 1, wherein an obliquely formed surface of the first end of the shaft is mirror-polished such that a light reflection surface is formed in the obliquely formed surface.

6. The motor according to claim 1, wherein an obliquely formed surface of the first end of the shaft is mirror-polished and a reflective film is formed on the obliquely formed surface such that a light reflection surface is formed in the obliquely formed surface.

7. The motor according to claim 1, wherein:
the shaft is formed of amorphous metal alloy,
the first end of the shaft is obliquely formed in an axial direction of the shaft such that a light reflection surface is formed in an obliquely formed surface of the shaft, and
a surface roughness Ry of the reflection surface is set to 0.4 μm or less.

8. The motor according to claim 1, wherein:
the shaft is formed of amorphous metal alloy,
the first end of the shaft is obliquely formed in an axial direction of the shaft,
a surface roughness Ry of an obliquely formed surface of the shaft is set to 0.4 μm or less, and
a reflective film is formed on the obliquely formed surface of the shaft such that a light reflection surface is formed in the obliquely formed surface.

9. An endoscope probe comprising the motor according to claim 1, wherein:
the motor is placed in the endoscope probe body such that the shaft or the output shaft projects in the direction opposite to the direction of the front end of the endoscope probe, and
the electric power supply wire led out to the outside of the motor is routed along the longitudinal direction of the endoscope probe.

10. A motor, comprising:
a magnet, a field coil, a housing having a first distal end and a second distal end, a first flange, an electric power supply wire, a shaft having a first end,
a lead wire led out from the field coil and connected to the electric power supply wire,
a cutout formed in the first distal end of the housing,
wherein the electric power supply wire connected with the lead wire is received along the cutout, and
a flat portion formed on an outer circumferential surface of the first flange, and the electric power supply wire is placed on the flat portion,
wherein the first flange on which the electric power supply wire is placed is fixed to the first distal end of the housing, and the electric power supply wire is led out to outside of the motor in a direction in which the shaft projects, which is toward the first distal end of the housing where the cutout is formed, and
the first end of the shaft, which projects from the first distal end of the housing and the first flange, is obliquely formed in an axial direction of the shaft.

11. The motor according to claim 10, further comprising a second flange fixed to the second distal end of the housing, wherein one or both of the flanges functions as a shaft bearing.

12. The motor according to claim 10, wherein the electric power supply wire is led out from one side of the outer circumference of the motor.

13. The motor according to claim 10, wherein at least a portion of the electric power supply wire is formed of a transparent electrode material.

14. The motor according to claim 10, wherein a reflective film is formed on an obliquely formed surface of the first end of the shaft such that a light reflection surface is formed in the obliquely formed surface.

15. The motor according to claim 10, wherein an obliquely formed surface of the first end of the shaft is mirror-polished such that a light reflection surface is formed in the obliquely formed surface.

16. The motor according to claim 10, wherein an obliquely formed surface of the first end of the shaft is mirror-polished and a reflective film is formed on the obliquely formed surface such that a light reflection surface is formed in the obliquely formed surface.

17. The motor according to claim 10, wherein:
the shaft is formed of amorphous metal alloy,
the first end of the shaft is obliquely formed in an axial direction of the shaft such that a light reflection surface is formed in an obliquely formed surface of the shaft, and
a surface roughness Ry of the reflection surface is set to 0.4 μm or less.

18. The motor according to claim 10, wherein:
the shaft is formed of amorphous metal alloy,
the first end of the shaft is obliquely formed in an axial direction of the shaft,
a surface roughness Ry of an obliquely formed surface of the shaft is set to 0.4 μm or less,
a reflective film is formed on the obliquely formed surface of the shaft such that a light reflection surface is formed in the obliquely formed surface.

19. A motor, comprising:
a magnet, a field coil, a housing, an electric power supply wire, a shaft,
a lead wire led out from the field coil is connected to the electric power supply wire,
a cutout is formed in an end of the housing,
the electric power supply wire connected with the lead wire is received along the cutout,
the motor further includes a reduction gear head,
a pinion is formed on an end of the shaft, and the gear head is driven by and connected to the motor via the pinion, and
the electric power supply wire is led out to the outside of the motor in a direction in which an output shaft of the gear head projects.

20. The motor according to claim 19, wherein an outer diameter of the gear head is less than that of the motor.

21. The motor according to claim 19, wherein:
a groove for receiving the electric power supply wire is formed in the housing of the gear head, and the electric power supply wire is received in the groove, and
the electric power supply wire is led out to the outside of the motor in the direction in which an output shaft of the gear head projects.

22. The motor according to claim 19, wherein:
an end of the output shaft is obliquely formed in an axial direction of the output shaft, and
a reflective film is formed on an obliquely formed surface of the output shaft such that a light reflection surface is formed in the obliquely formed surface.

23. The motor according to claim 19, wherein:
an end of the output shaft is obliquely formed in an axial direction of the output shaft, and
an obliquely formed surface of the output shaft is mirror-polished such that a light reflection surface is formed in the obliquely formed surface.

24. The motor according to claim 19, wherein:
an end of the output shaft is obliquely formed to the axial direction of the output shaft, and
an obliquely formed surface of the output shaft is mirror-polished and a reflective film is formed on the obliquely formed surface such that a light reflection surface is formed in the obliquely formed surface.

25. The motor according to claim 19, wherein:
the overall output shaft is formed of amorphous metal alloy,
an end of the output shaft is obliquely formed in an axial direction of the output shaft such that a light reflection surface is formed in an obliquely formed surface of the output shaft, and
a surface roughness Ry of the reflection surface is set to 0.4 μm or less.

26. The motor according to claim 19, wherein:
the overall output shaft is formed of amorphous metal alloy,
an end of the output shaft is obliquely formed in an axial direction of the output shaft,
a surface roughness Ry of an obliquely formed surface of the output shaft is set to 0.4 μm or less, and
a reflective film is formed on the obliquely formed surface of the output shaft such that a light reflection surface is formed in the obliquely formed surface.

27. A motor comprising:
a magnet, a field coil, a housing, a flange, an electric power supply wire, a shaft,
a lead wire led out from the field coil is connected to the electric power supply wire,
a cutout is formed in an end of the housing,
the electric power supply wire connected with the lead wire is received along the cutout,
a flat portion is formed on an outer circumferential surface of the flange, and the electric power supply wire is placed on the flat portion,
the flange on which the electric power supply wire is placed is fixed to an end of the housing,
the motor further includes a reduction gear head,
a pinion is formed on an end of the shaft, and the gear head is driven by and connected to the motor via the pinion, and
the electric power supply wire is led out to the outside of the motor in a direction in which an output shaft of the gear head projects.

28. The motor according to claim 27, wherein an outer diameter of the gear head is less than that of the motor.

29. The motor according to claim 27, wherein:
a groove for receiving the electric power supply wire is formed in the housing of the gear head, and the electric power supply wire is received in the groove, and
the electric power supply wire is led out to the outside of the motor in the direction in which an output shaft of the gear head projects.

30. The motor according to claim 27, wherein:
an end of the output shaft is obliquely formed in an axial direction of the output shaft, and
a reflective film is formed on an obliquely formed surface of the output shaft such that a light reflection surface is formed in the obliquely formed surface.

31. The motor according to claim 27, wherein:
an end of the output shaft is obliquely formed in an axial direction of the output shaft, and
an obliquely formed surface of the output shaft is mirror-polished such that a light reflection surface is formed in the obliquely formed surface.

32. The motor according to claim 27, wherein:
an end of the output shaft is obliquely formed to the axial direction of the output shaft, and
an obliquely formed surface of the output shaft is mirror-polished and a reflective film is formed on the obliquely formed surface such that a light reflection surface is formed in the obliquely formed surface.

33. The motor according to claim 27, wherein:
the overall output shaft is formed of amorphous metal alloy,
an end of the output shaft is obliquely formed in an axial direction of the output shaft such that a light reflection surface is formed in an obliquely formed surface of the output shaft, and
a surface roughness Ry of the reflection surface is set to 0.4 μm or less.

34. The motor according to claim 27, wherein:
the overall output shaft is formed of amorphous metal alloy,
an end of the output shaft is obliquely formed in an axial direction of the output shaft,
a surface roughness Ry of an obliquely formed surface of the output shaft is set to 0.4 μm or less, and
a reflective film is formed on the obliquely formed surface of the output shaft such that a light reflection surface is formed in the obliquely formed surface.

35. An endoscope probe, comprising:
a motor including a magnet, a field coil, a housing, an electric power supply wire, a shaft,
a lead wire led out from the field coil is connected to the electric power supply wire, and
a cutout is formed in an end of the housing,
wherein the electric power supply wire connected with the lead wire is received along the cutout and led out to the outside of the motor in a direction in which the shaft projects, and
wherein
the motor is placed in the endoscope probe body such that the shaft or the output shaft projects in the direction opposite to a direction of a front end of the endoscope probe, and
the electric power supply wire led out to the outside of the motor is routed along a longitudinal direction of the endoscope probe.

36. An endoscope probe, comprising:
a motor including a magnet, a field coil, a housing, a flange, an electric power supply wire, a shaft,
a lead wire led out from the field coil is connected to the electric power supply wire,
a cutout is formed in an end of the housing,
wherein the electric power supply wire connected with the lead wire is received along the cutout,
a flat portion is formed on an outer circumferential surface of the flange, and the electric power supply wire is placed on the flat portion, and
the flange on which the electric power supply wire is placed is fixed to an end of the housing, and the electric power supply wire is led out to the outside of the motor in a direction in which the shaft projects; and,
wherein
the motor is placed in the endoscope probe body such that the shaft or the output shaft projects in the direction opposite to a direction of the front end of the endoscope probe, and
the electric power supply wire led out to the outside of the motor is routed along a longitudinal direction of the endoscope probe.

* * * * *